(12) United States Patent
Anderson et al.

(10) Patent No.: US 10,023,512 B2
(45) Date of Patent: *Jul. 17, 2018

(54) PRODUCTION OF ORGANIC MATERIALS USING OXIDATIVE HYDROTHERMAL DISSOLUTION METHOD

(75) Inventors: Kenneth B. Anderson, Carbondale, IL (US); John C. Crelling, Carbondale, IL (US); William W. Huggett, Carbondale, IL (US); Derek M. Perry, Carbondale, IL (US)

(73) Assignee: SOUTHERN ILLINOIS UNIVERSITY CARBONDALE, Carbondale, IL (US)

(*) Notice: Subject to any disclaimer, the term of this patent is extended or adjusted under 35 U.S.C. 154(b) by 1071 days.

This patent is subject to a terminal disclaimer.

(21) Appl. No.: 13/488,092

(22) Filed: Jun. 4, 2012

(65) Prior Publication Data

US 2012/0289695 A1    Nov. 15, 2012

Related U.S. Application Data

(63) Continuation-in-part of application No. 13/148,237, filed as application No. PCT/US2010/023886 on Feb. 11, 2010, now Pat. No. 8,563,791.

(Continued)

(51) Int. Cl.
| | | |
|---|---|---|
| C07G 17/00 | (2006.01) |
| C07C 27/00 | (2006.01) |
| C07C 67/00 | (2006.01) |
| C07C 37/54 | (2006.01) |
| C07C 41/01 | (2006.01) |
| C07C 51/21 | (2006.01) |
| C10G 1/04 | (2006.01) |

(52) U.S. Cl.
CPC ............ C07C 27/00 (2013.01); C07C 37/54 (2013.01); C07C 41/01 (2013.01); C07C 51/21 (2013.01);
(Continued)

(58) Field of Classification Search
CPC . Y02E 50/10; Y02E 50/30; C10L 5/44; C10L 9/086
See application file for complete search history.

(56) References Cited

U.S. PATENT DOCUMENTS 2,665,249 A * 1/1954 Zimmermann ......... C02F 11/08
                                                    162/31
5,326,456 A   7/1994 Brons et al.
(Continued)

FOREIGN PATENT DOCUMENTS

JP        64-075591      3/1989
JP     2003-236491 A     8/2003
(Continued)

OTHER PUBLICATIONS

Supplementary European Search Report issued by the European Patent Office in European Patent Application No. EP 12 79 3493 dated Oct. 3, 2014.
(Continued)

*Primary Examiner* — Ellen M McAvoy
*Assistant Examiner* — Ming Cheung Po
(74) *Attorney, Agent, or Firm* — Polsinelli PC

(57) ABSTRACT

Methods of producing organic materials, and in particular methods of producing petroleum materials and organic compounds such as aromatic acids, phenols, and aliphatic poly-carboxylic acids using an oxidative hydrothermal dissolution (OHD) process are disclosed.

21 Claims, 19 Drawing Sheets

Related U.S. Application Data

(60) Provisional application No. 61/151,677, filed on Feb. 11, 2009.

(52) U.S. Cl.
CPC .............. *C07C 67/00* (2013.01); *C10G 1/047* (2013.01); *C10G 2300/1011* (2013.01); *C10G 2300/805* (2013.01); *Y02P 30/20* (2015.11)

(56) References Cited

U.S. PATENT DOCUMENTS

| | | | | |
|---|---|---|---|---|
| 5,560,823 | A | * | 10/1996 | Whiting .................. B01J 3/008 210/175 |
| 5,997,751 | A | * | 12/1999 | Higo ......................... B01J 3/00 210/758 |
| 6,001,256 | A | * | 12/1999 | Hawthorne ............... B09C 1/02 210/633 |
| 6,103,129 | A | * | 8/2000 | Bond .................... C02F 11/086 210/721 |
| 7,259,257 | B2 | | 8/2007 | Schlesiger et al. |
| 7,692,050 | B2 | | 4/2010 | Adams et al. |
| 2002/0003115 | A1 | * | 1/2002 | Conaway ................. B03B 9/02 210/759 |
| 2003/0168381 | A1 | | 9/2003 | Hokari et al. |
| 2004/0192980 | A1 | | 9/2004 | Appel et al. |
| 2004/0232046 | A1 | | 11/2004 | Tanaka et al. |
| 2007/0144941 | A1 | | 6/2007 | Hokari et al. |
| 2008/0283472 | A1 | | 11/2008 | Scott et al. |
| 2010/0108567 | A1 | | 5/2010 | Medoff |

FOREIGN PATENT DOCUMENTS

| | | |
|---|---|---|
| JP | 2003-236569 A | 8/2003 |
| JP | 2007-296440 | 11/2007 |
| WO | WO1981000854 A1 * | 4/1981 |
| WO | WO2010093785 | 8/2010 |

OTHER PUBLICATIONS

Abeln, et al., "Supercritical Water Oxidation (SCWO): A process for the treatment of industrial waste effluents," High pressure res., 20(1) 2001, pp. 537-547.

Veriansyah, et al., "Supercritical water oxidation for the destruction of toxic organic wastewaters: A review," Journal of Environmental Sciences, 19(2007) pp. 513-522.

Official Action for Russian Patent Application No. 2011137401 dated Nov. 7, 2013 (translation included).

Second Office Action for CN 201080007889.6 entitled Process for the Dissolution of Coal, Biomass and Other Organic Solids in Superheated Water, dated Jan. 2, 2014.

Third Office Action for CN 201080007889.6 entitled Process for the Dissolution of Coal, Biomass and Other Organic Solids in Superheated Water, dated Apr. 3, 2014.

Office Action issued by the Canadian Patent Office in Canadian Patent Application No. 2,751,583 dated Apr. 10, 2014.

Williams, et al., Subcritical and Supercritical Water Gasification of Cellulose, Starch, Glucose and Biomass Waste, Energy and Fules, Apr. 12, 2006, vol. 20, No. 3, pp. 1259-1265.

Siskin, et al., Reactivity of Organic Compounds in Superheated Water: General Background, Chemical Reviews, Apr. 2001, vol. 101, iss. 4, pp. 825-835, www.ncbi.nim.nih.gov/pubmed/11709859.

International Search Report and Written Opinion for International Application No. PCT/US12/40746 dated Aug. 28, 2012.

Supplementary European Search Report for European Application No. EP10741721 dated Feb. 7, 2012.

International Search Report for Application No. PCT/US2010/023886 dated Sep. 20, 2010.

Examination Report issued in corresponding Australian Application No. 2012261870 dated Jul. 15, 2016. 4 pages.

Anderson et al., "Oxidative Hydrothermal Dissolution of Illinois Coal," Final Technical Report, Sep. 1, 2005 through Oct. 31, 2005. 2 pages.

Japanese Office Action from Japanese Patent Application No. 2011-550227, dated May 12, 2015,with English translation, 4 pages.

Australian Patent Examination Report No. 1 in corresponding Australian Patent Application No. 2012261870, 3 pages, dated Apr. 29, 2016.

Chinese Office Action in corresponding Chinese Patent Application No. 201280026415.5, 7 pages, dates Mar. 16, 2016.

English translation of Japanese Office Action in corresponding Japanese Patent Application No. 2014-513791, 4 pages, dated Apr. 26, 2016.

New Zealand Further Examination Report in corresponding New Zealand Patent Application No. 708844, 2 pages, dated Feb. 23, 2016.

Office Action issued in correspondence Japanese Application No. 2011-550227, dated Sep. 6, 2016, 11 pages.

\* cited by examiner

PRODUCTION OF ORGANIC MATERIALS USING OXIDATIVE HYDROTHERMAL DISSOLUTION METHOD

CROSS-REFERENCE TO RELATED APPLICATION

This application is a Continuation-in-Part of Non-Provisional application Ser. No. 13/148,237 filed on Aug. 5, 2011, which is a US National Application of PCT Application No. PCT/US10/23886 filed on Feb. 11, 2010, which claims priority to Provisional Application Ser. No. 61/151,677, filed on Feb. 11, 2009, all of which are hereby incorporated by reference herein in their entirety. This application further claims priority to Provisional Application Ser. No. 61/492,910, filed on Jun. 3, 2011, which is hereby incorporated by reference herein in its entirety.

FIELD

This document relates to methods of producing organic materials, and in particular to methods of producing petroleum materials and organic compounds such as aromatic acids, phenols, and aliphatic poly-carboxylic acids using an oxidative hydrothermal dissolution (OHD) process.

BACKGROUND

The majority of raw materials used by the chemical industry for the production of polymers and other purposes are typically derived from petroleum sources. The cost and availability of these raw materials are heavily influenced by the available petroleum supplies, which have been generally dwindling for approximately the last decade due to peaking world production capacity and increasing world demand. Because the global petroleum supply is a non-renewable resource, the future availability of petroleum and of raw materials derived from petroleum is not expected to improve.

As recoverable reserves of conventional petroleum become increasingly scarce and expensive to recover, interest in the recovery of heavy oil resources, such as bituminous sands (also known as oil sands and/or tar sands), is increasing. By some estimates, amounts of oil in place in known bituminous sand deposits may be larger than all remaining worldwide conventional petroleum reserves and is at least of the same order of magnitude as all remaining worldwide conventional petroleum reserves. However recovery of these resources is difficult and subject to numerous undesirable environmental consequences.

Oxidative hydrothermal dissolution (OHD) technology is an environmentally friendly technology that breaks down macromolecular organic materials using an oxidative bond cleavage process resulting in the generation of organic compounds such as low molecular weight aromatic and aliphatic acids, phenols, and other products. This application describes methods of using OHD technology to break down macromolecular and heterogeneous materials such as bituminous sands, coal, lignocellulosic biomass, and kerogen to produce specific products that are currently used or are potentially useful to the chemical industry, as well as other products.

SUMMARY

In one embodiment, a process for solubilizing an organic solid contained within a composite material including an organic solid and an inorganic matrix may include contacting the composite material with an oxidant in superheated water to form an aqueous mixture comprising at least one solubilized organic solute.

In some embodiments, the process may further include pulverizing the composite material and combining the pulverized composite material with water to form a slurry prior to contacting the composite material with the oxidant in the superheated water.

In some embodiments, the oxidant is molecular oxygen ($O_2$), wherein the molecular oxygen is supplied by any known method of supplying, producing, or separating molecular oxygen from any known mixture in any form. Non-limiting examples of methods of obtaining a supply of molecular oxygen include: in situ decomposition of hydrogen peroxide; fractional distillation of liquefied air; electrolysis of water; transfer from a stored oxygen supply; membrane separation from air; and any combination thereof.

In some embodiments, the composite material may be selected from the group consisting of coal, bituminous sand, carbonaceous shale, and any mixture thereof.

In some embodiments, the composite material may be contacted with the oxidant in the superheated water within a reactor, wherein the composite material, oxidant, and superheated water are maintained in a non-gaseous phase to inhibit the formation of a head space within the reactor.

In some embodiments, the process may further include chilling the aqueous mixture to a temperature of about 20° C.

Additional objectives, advantages and novel features will be set forth in the description that follows or will become apparent to those skilled in the art upon examination of the drawings and detailed description which follows.

BRIEF DESCRIPTION OF THE DRAWINGS

The following figures illustrate various aspects for a process of producing organic materials using an oxidative hydrothermal dissolution process.

Corresponding reference characters indicate corresponding elements among the various views of the drawings. The headings used in the figures should not be interpreted to limit the scope of the claims.

DETAILED DESCRIPTION

Figure 1:
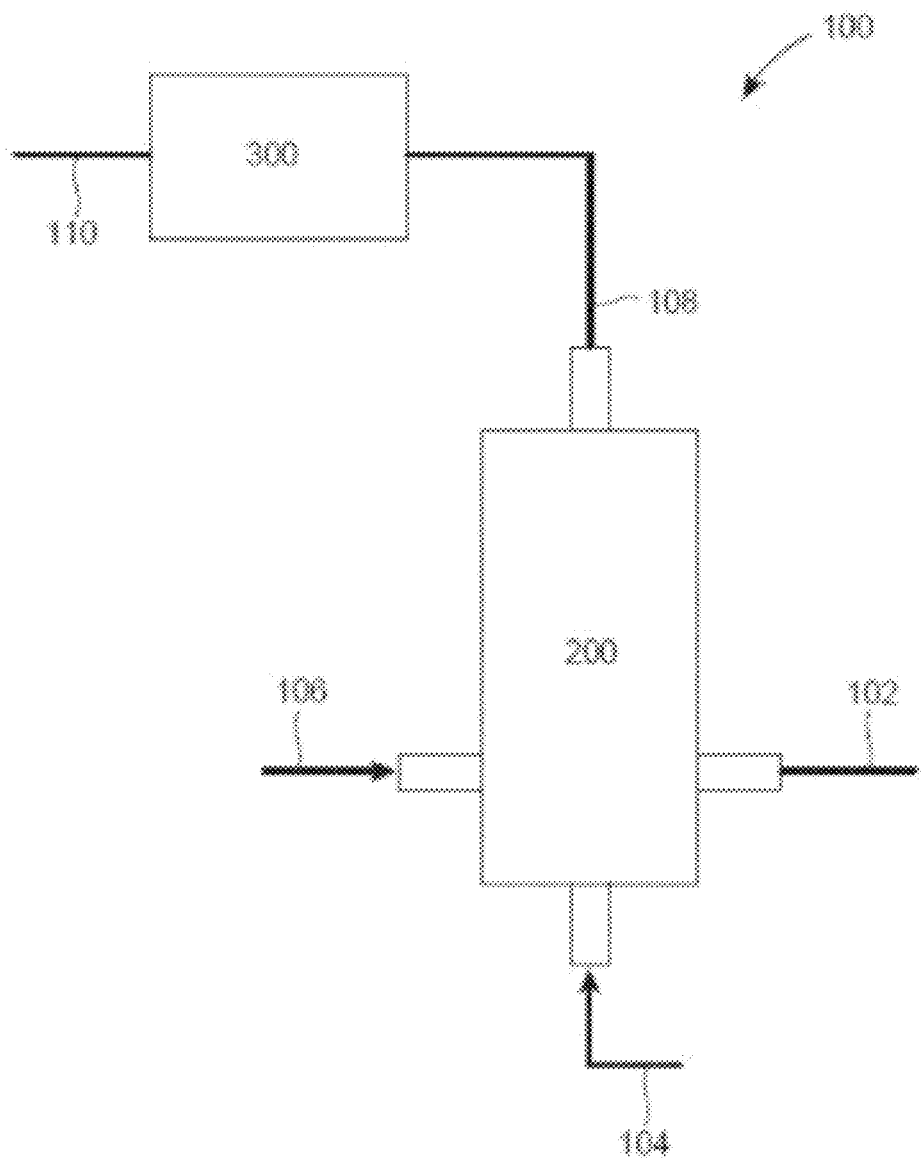
FIG. 1 is a schematic of an oxidative hydrothermal dissolution (OHD) process.

The invention relates generally to methods of producing water-soluble products from organic solids using an oxidative hydrothermal dissolution (OHD) method. Certain aspects of the OHD method are described in detail in PCT Application Number PCT/US10/23886, which is hereby incorporated in its entirety herein.

As described herein, the term "biomass" may include, but not limited to, materials containing cellulose, hemicellulose, lignin, protein and carbohydrates such as starches and sugars, trees, shrubs and grasses, corn, and corn husks, municipal solid waste including materials related to waste that is normally disposed of by occupants of residential dwelling units, commercial establishments and industry, biomass high in starch, including starch, sugar or protein such as corn, grains, fruits and vegetables, branches, bushes, canes, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods, organic waste materials generated from agricultural processes including framing and forestry activities such as forestry wood waste, virgin biomass and/or non-virgin biomass including agricultural biomass, commercial organics, construction and demolition debris, paper, cardboard, scrap wood, saw dust, and plastics.

As used herein, the term "aqueous mixture" shall mean a homogeneous mixture of one or more substances (solutes) dispersed molecularly in a sufficient quantity of dissolving medium (solvent).

As used herein, the term "composite material" shall mean a combination of two or more constituent materials of different physical or chemical properties which remain separate and distinct in the final structure. For example, the composite material may include an organic solid and an inorganic matrix.

I. Oxidative Hydrothermal Dissolution

The OHD method includes contacting an organic solid with an oxidant in a reactor containing superheated water to form at least one solubilized organic solute. The reaction breaks down the macromolecular structure of the organic solid, which would otherwise not be soluble in water, into lower molecular weight fragments. These lower molecular weight fragments are soluble in water. These water-soluble fragments are referred to as dissolved organic solids, solubilized organics, or solubilized organic solutes. The solubilized fragments can then be used as raw materials for various chemical processes or as liquid fuels. In one aspect, if the solubilized fragments are dissolved carbohydrates such as low molecular weight sugars or oxidized low molecular weight sugars, the dissolved carbohydrates may be fermented to produce alcohols or used in other processes to produce a variety of other products.

Non-limiting examples of organic solids suitable for processing using the OHD method include coal, bituminous sand, lignite, kerogen, biomass, and solid organic wastes. Biomass, as defined herein, refers to biological material derived from living organisms and includes, for example, plant-based materials such as wood, grasses, and grains. For example, a solid organic waste may be waste plastics. Coal, for example, has a complex, high molecular weight macromolecular structure made up of numerous cross-linked aromatic and aliphatic sub-structures. It is believed that coal is insoluble in water primarily because of the extent of cross-linking present between different parts of this structure. Disruption of cross-linking structural elements in organic solids breaks the structure into smaller sub-structural units. For example, coal may be converted into a new product with modified physical properties using OHD methods. In addition, the OHD method may be used to convert biomass into soluble organics. For example, biomass containing cellulose, hemicellulose, and/or lignins may be converted into dissolved low molecular weight sugars or oxidized low molecular weight sugars, and other products.

The oxidant can be any oxidant capable of oxidizing the organic solid, including but not limited to molecular oxygen ($O_2$). The use of molecular oxygen as an oxidant avoids the use of exotic oxidants, such as permanganates, chromate oxides, or organic peroxides that may be harmful to the environment or expensive. The molecular oxygen may be supplied by any known method of supplying, producing, or separating molecular oxygen from any known mixture in any form. Non-limiting examples of methods of obtaining a supply of molecular oxygen include: in situ decomposition of hydrogen peroxide; fractional distillation of liquefied air; electrolysis of water; transfer from a stored oxygen supply; membrane separation from air; and any combination thereof. Non-limiting examples of suitable stored oxygen supplies include pressurized oxygen tanks. The addition of the oxidant to the superheated water increases the rate of conversion and the overall percent conversion of the organic solid to solubilized products.

The reaction media in the OHD method may be superheated water having a temperature from about 100° C. to about 374° C. In other embodiments, the superheated water may have a temperature ranging from about 200° C. to about 350° C.

The pressure in the reactor may be specified to be sufficient to maintain the water in a liquid state (without water loss into a gas phase). The pressure may range from about 100 kPa (kiloPascal) to about 22 MPa (megaPascal) in one embodiment. In other embodiments, the pressure may range from about 1.5 MPa to about 17 MPa, and from about 12 MPa to about 16 MPa. The terms "hydrothermal water" and "superheated water" may be used interchangeably throughout the specification.

Without being limited to any particular theory, it is believed that the oxidation reaction is a surface reaction of the oxidant and the organic solid surface. Therefore, maintaining a sufficiently high surface-area-to-volume ratio of the organic solid may enhance the rate of the reaction. The organic solid may have a small particle size to provide greater surface area per volume for the reaction. However, the organic solid may be any size without impeding the progression of the reaction. The reaction may begin at the surface of the organic solid and etches away the surface until the solid is dissolved or until the reaction is halted.

The OHD method may also include the addition of other components to the reaction, including but not limited to pH modifiers, catalysts, additional solvents, and any combination thereof. It is contemplated that these additives may promote the formation of particular desired products or minimize the formation of undesired products.

The process may optionally further include chilling the solubilized organic solute. One advantage of chilling the solubilized organic solute may be to prevent further oxidation of the solubilized organic solute. The solubilized organic solute may be chilled to room temperature or approximately 20° C. However, further processing, such as distillation, evaporation, or further reaction of the dissolved organics, may not require cooling, and chilling may not be desirable.

FIG. 1 is a schematic diagram of the OHD process 100. An organic solid may be loaded into a reactor 200. The reactor 200 may be an up-flow reactor with no gaseous head space to enhance the efficiency of the OHD method. Superheated water may be introduced into the reactor 200 through a port 102 until equilibration is reached. An oxidant, for example, molecular oxygen, may be introduced into the reactor 200 through a port 104. Molecular oxygen may be supplied directly from a storage tank, separated from the surrounding air, or molecular oxygen may be generated by a chemical process such as the thermal decomposition of hydrogen peroxide prior to addition to the reactor 200. A port 106 may be used to introduce any other components added to the reaction, including, but not limited to, pH modifiers, catalysts, or organic solvents. The solubilized organic solute resulting from the organic solid exits the reactor 200 from a port 108 and may optionally enter a chiller 300. The cooled effluent from a port 110 may be monitored for the presence of solubilized organic solute or may be collected for further processing or analysis. Non-limiting examples of suitable analysis techniques for the cooled effluent include photodiode array detection (PDA), GC-MS, and any combination thereof. The OHD process may be conducted as a batch, semi-continuous, or continuous process.

The raw product (OHD liquor) derived from the processing of organic matter using OHD methods may be an aqueous solution of dissolved organic products. In some aspects, depending on the particular organic matter processed and OHD process conditions, the OHD liquor may be a clear solution and does not contain suspended colloidal solids. In other aspects, the OHD liquor may include suspended particles. Non-limiting examples of suspended particles include inorganic particles such as inorganic matrix, unreacted organic solids, and any combination thereof. For example, if OHD process conditions do not result in the complete conversion of organic solids into solubilized organic solids, the OHD liquor may include suspended particles of unreacted organic solid; in this example, the OHD process may include too low of an oxidant concentration and/or too brief of a reaction time.

Without being limited to any particular theory, the formation of the OHD liquor product is not the result of simple hydrolysis. Based on previous observations (not shown herein) production of the dissolved product is directly related to the delivery of $O_2$ and the response of the reactor to delivery of the oxidant is rapid.

The OHD methods may be applied to a wide range of organic materials, including, but not limited to, coal, carbonaceous shales, organic-rich carbonate rocks, bituminous sands, lignocellulosic and other biomass as described herein above, lignite, bituminous coal, anthracite and wood charcoal. Complete conversion of organic materials to soluble products may be readily achieved using the OHD method, although rates of reaction may vary considerably.

Reaction rate may depend on particle size, reaction temperature, oxidant loading and flow rate/contact time, as well as varying the choice of organic material used as the initial substrate. Typically, the reaction proceeds in a matter of minutes for the complete dissolution of bituminous coal particles having a particle size ranging from about 60 mesh to 20 mesh. In general, low rank materials react faster than high rank materials, (presumably due to the more polycondensed nature of the high rank materials), and macerals react in order of structure (fastest to slowest): liptinite>vitrinite>inertinite.

The OHD method likely works by oxidative cleavage of labile structures, resulting in the disruption of the overall macromolecular structure. As low molecular weight products are produced, they are dissolved into the reaction medium (water), which at hydrothermal conditions functions as an excellent solvent for most organic compounds. The dissolved organics are separated from residual solid, thereby exposing fresh substrate surface for subsequent reaction with additional oxidant. Rapid removal of the water and separation of the produced organic solute or quenching prevents over-oxidation of the dissolved organic compounds in the OHD liquor product.

For most raw solid organic matter, from about 70% to 100% of the initial carbon is recovered as solubilized products at optimal reaction conditions. Minor amounts of gaseous products (CO and $CO_2$) may also be generated. Typically, no gaseous N or S oxides are generated. Inorganic N and S are retained in the aqueous phase as sulfate and nitrate, respectively. Organic S is at least partially retained as soluble organo-sulfur compounds in the OHD liquor product.

Characterization of the solubilized products indicates that the OHD liquor product typically consists of moderately complex mixtures of low molecular weight organics. For bituminous coal, these consist predominantly of: (i) aliphatic carboxylic acids and diacids from C1 to about C20; and (ii) mono-aromatic carboxylic acids, polyacids and phenols, including methoxylated analogs. In many cases acetic acid is the single most abundant product obtained and may account for up to about 5% of the raw product, depending on the initial feedstock processed using the OHD method. In an embodiment, one or more specific organic compounds may be isolated or purified from the OHD liquor product using any known method of refining such as fractional distilling and others.

OHD products derived from biomass tend to be simpler mixtures of organic compounds compared to OHD products derived from coals. Non-limiting examples of OHD products derived from biomass include mixtures of low molecular weight sugars including glucose, fructose, galactose, sucrose, maltose, lactose, oxidized low molecular weight sugars, and any combination thereof. Non-limiting examples of oxidized low molecular weight sugars include keto, aldo, and carboxy derivatives of any of the low molecular weight sugars described herein above. Without being limited to any particular theory, cellulose, hemicellulose, and other macromolecular carbohydrates may be broken down by the OHD process via hydrolysis and oxidative cleavage to produce these. Other specific mixtures of organic compounds contained in the OHD liquor products derived from various organic materials in other aspects are illustrated herein below in the Examples.

II. Oxidative Hydrothermal Dissolution Devices

Figure 2:
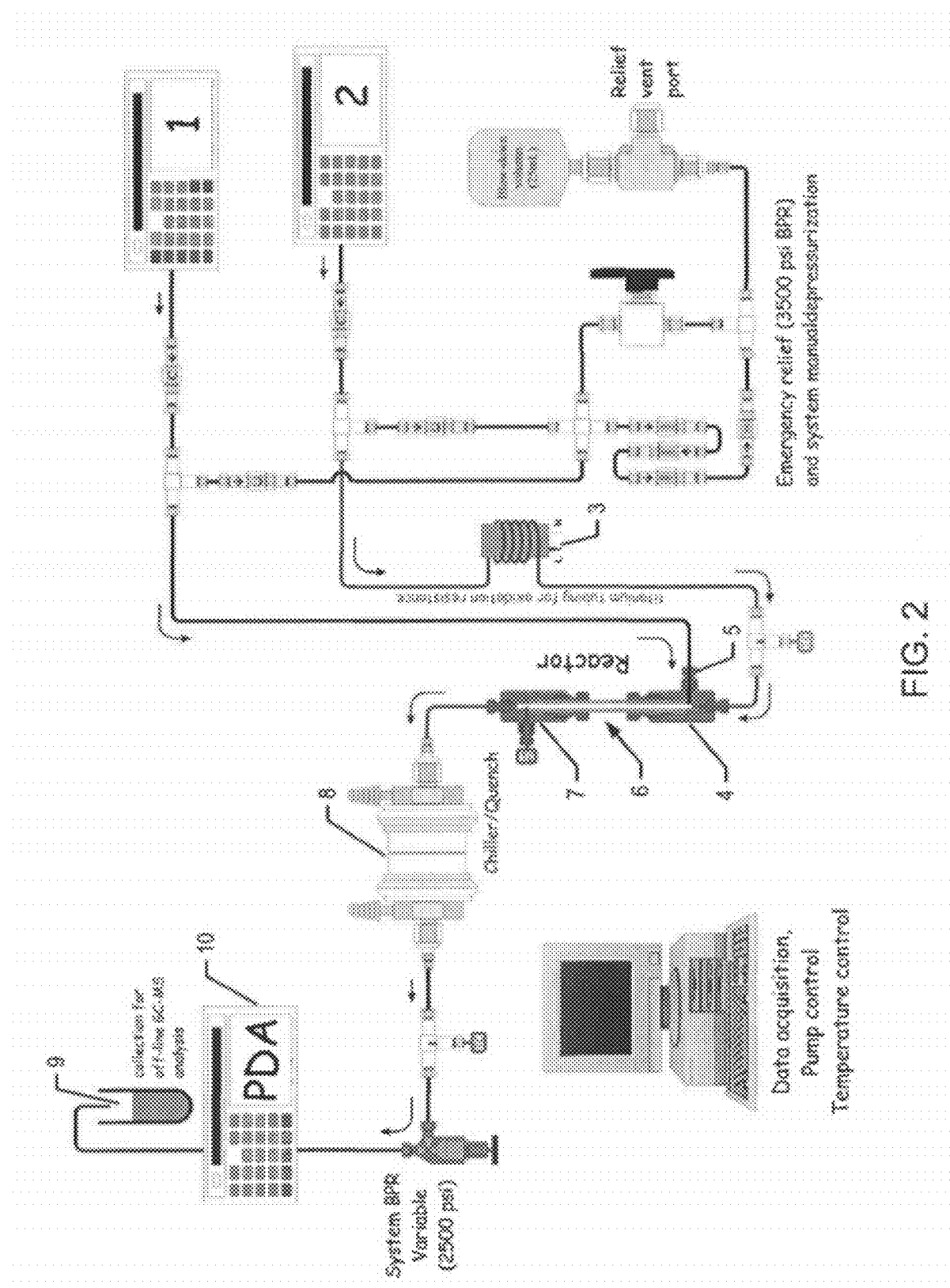
FIG. 2 is a schematic illustration of a semi-continuous micro reactor system used for testing and evaluation of the OHD process.

An embodiment of a semi-continuous flow OHD device is illustrated schematically in FIG. 2. An organic solid may be loaded into a reactor 6 and superheated water and an oxidant may be introduced into the reactor 6 by pumps 1 and 2. If the oxidant is derived from hydrogen peroxide, hydrogen peroxide may be decomposed in a heater 3, and the resulting molecular oxygen and superheated water may enter the reactor via ports 4 and 5 respectively. Additional components or water may be introduced into the reactor 6 via a port 7. A reaction between the organic solid and the oxidant takes place in the reactor 6 and generates a solubilized organic solute, which leaves the reactor 6 and optionally enters a chiller 8. Effluent may collected in a vessel 9, and data are collected by a detector 10.

Figure 3:
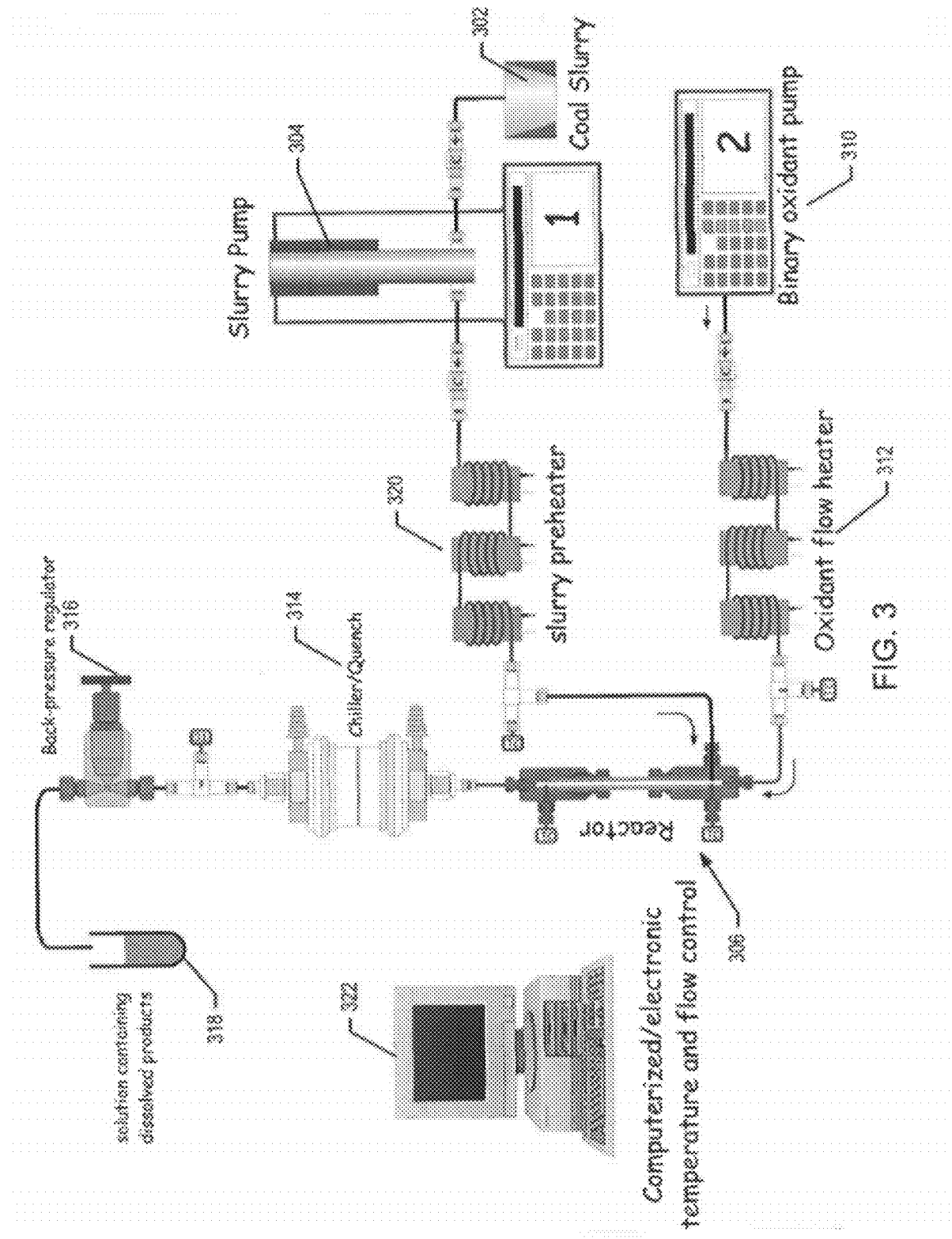
FIG. 3 is a schematic illustration of a continuous micro reactor system used for testing and evaluation of the OHD process.

An embodiment of a continuous flow OHD device is illustrated schematically in FIG. 3. An organic solid such as coal, bituminous sand, or carbonaceous shale, in which the inorganic component of the shale may comprise minerals including but not limited to silicates or carbonates, may be used as a feedstock to the OHD device. The feedstock may be pulverized in a mill 302 and combined with water to form a slurry in a slurry generator 304. The mill 302 and the slurry generator 304 may be combined into a single operation by a process such as wet milling. The slurry may then be pumped into a reactor 306 by a slurry pump 308. The slurry may be heated before entering the reactor 306 using a preheater 320. An oxidant, such as molecular oxygen, and superheated water may be introduced into the reactor 306 by a pump 310. If the molecular oxygen is derived from hydrogen peroxide, the hydrogen peroxide may be decomposed in a heater 312 and molecular oxygen and superheated water may then enter the reactor 306. A reaction between the organic solid and the oxidant may take place in the reactor 306 and generate a solubilized organic solute. The solubilized organic solute may exit the reactor 306 and may optionally enter a chiller 314. Back pressure may be controlled by a back-pressure regulator 316. Effluent may be collected in a vessel 318. Wiring and control details have been omitted, but are implicit in the design of the reactor system. This system may be operated continuously, and the temperature and flow rate of reactants may be controlled automatically by a computer 322 or other data processing device.

III. Extraction of Petroleum Materials from Bituminous Sands or Oil Shales Using OHD Methods The OHD methods described above herein may be used to recover petroleum materials from bituminous sands or oil shales in other embodiments. The particular device, operating systems, and reactants used to recover the petroleum materials in this embodiment may vary depending on the nature and location of the deposit in which the bituminous sands or oil shales occur and desired petroleum materials to be extracted.

Large bituminous sand deposits occur in several locations, but two predominant known reserves are the Athabasca Oil Sands in Alberta, Canada and the Orinoco oil sands (Venezuela). Between them, the Canadian and Venezuelan deposits contain about 3.6 trillion barrels ($570 \times 10^9$ m$^3$) of recoverable oil, compared to 1.75 trillion barrels ($280 \times 10^9$ m$^3$) of conventional oil worldwide. These oil sand deposits may include as much as two-thirds of total remaining global recoverable petroleum resources. In addition to recovering the petroleum materials from bituminous sands, the OHD methods may also be used in the context of environmental remediation, including but not limited to the cleanup of oily sand resulting from an oil spill from an oil tanker or other ocean vessel, an oil production facility, or an oil refinement facility.

Specific examples of the recovery of petroleum products using OHD methods are described in the Examples provided herein below.

III. Production of Aromatic Acids, Phenols, and Aliphatic Acids Using OHD Methods The OHD methods described above herein may be used to produce useful raw materials and other organic compounds for the chemical industry, including but not limited to aromatic acids, phenols, and aliphatic acids. The particular device, operating systems, and reactants used to produce the raw materials and other organic compounds may vary depending on the particular organic solid materials from which the feedstocks to the OHD device are produced, as well as the desired organic compound products to be produced using the OHD method. Non-limiting examples of organic matter suitable for use as a feedstock in the OHD method in this embodiment include coal, carbonaceous shales, organic-rich carbonate rocks, bituminous sands, lignocellulosic biomass, lignite, bituminous coal, anthracite, wood charcoal, and kerogen. "Kerogen", as used herein, refers to a mixture of organic chemical compounds that make up a portion of the organic matter in sedimentary rocks, including but not limited to oil shale.

Table 1 is a listing of non-limiting examples of organic compounds that may be produced using the OHD method described herein above.

TABLE 1

ORGANIC COMPOUNDS PRODUCED USING OHD METHODS

| Compound | Chemical Structure |
|---|---|
| 1 p-hydroxyl benzoic acid and related hydroxylated and methoxylated analogs | (structure) |
| 2 Benzene dicarboxylic acids, various isomers, and related hydroxylated and methoxylated analogs | (structure) |
| 3 Aliphatic keto-acids | (structure) |
| 4 Benzene tricarboxylic acids and various isomers | (structure) |
| 5 Benzene tetracarboxylic acids and various isomers | (structure) |
| 6 Aliphatic dicarboxylic acids | (structure) |
| 7 p-coumaric acid and related hydroxylated and methoxylated analogs | (structure) |

Note:
$R_1$ = H or OH or OCH$_3$, $R_2$ = H or OH, or OCH$_3$, $R_3$ = H or CH$_3$, and n is an integer between 1 and about 30 or more.

In order to be of value on a large scale, the organic compounds obtained from the OHD methods may be recoverable in high yield. The yields of the OHD processing may be measured by assessing the removal of organics from an inorganic matrix, especially in those cases in which bituminous sand is processed using the OHD method. For OHD feedstocks comprising a significant amount of inorganic phase, such as bituminous sands or carbonaceous shales, the yield of OHD processing may be measured as the residual carbon retained in the inorganic phase after OHD processing or as the overall mass loss resulting from high-temperature ashing or combustion after OHD processing. Low amounts of residual carbon remaining in the inorganic matrix may be desirable, because this indicates that most or all of the bituminous material has been removed from the inorganic matrix resulting in "cleaner" sand or other inorganic matrix that may be returned to the environment. In addition, potentially more of the bituminous product may be recovered for refining into organic compounds.

Another method of assessing the yield of organic compounds after OHD processing may include measuring the amount of carbon contained within the aqueous phase or OHD liquor resulting from the processing of the organic matter in the reactor in an OHD process. The yield may be quantified as the % of the initial carbon contained in the organic matter that is recovered as dissolved product in the aqueous phase or OHD liquor. High yields of carbon in the dissolved product may be desirable, because this indicates that the aqueous phase contains a large proportion of the original bituminous material that may be recovered and refined into organic compounds. Carbon not recovered and not retained in the inorganic residue may be lost as gaseous products. Typically in OHD processes the gaseous products may include CO with some $CO_2$. CO may be recovered as a useful by-product, but typically minimal gas production is desirable.

Specific examples of useful raw materials and other organic compounds produced using the OHD method to break down organic matter such as coal, lignocellulosic biomass, and kerogen are provided herein below in the Examples.

EXAMPLES

Example 1: OHD Processing of Canadian Athabasca Oil Sands

A bituminous sand sample of Athabasca oil sand was processed using the OHD method described herein above. For comparative proposes, to evaluate the relative efficacy of OHD for separation and recovery of organic materials from the inorganic matrix, the raw sand was compared with products produced by hot water extraction (to approximately simulate current extraction technologies, exhaustive laboratory extraction with organic solvents, and OHD. Both soluble and insoluble products were recovered after processing by each method and analyzed. Insoluble products were analyzed for carbon content and high temperature ash yield, to determine the efficiency of removal of the organic bitumen. Soluble products were recovered and analyzed to investigate the nature of the organic materials recovered by each method.

Figure 4:
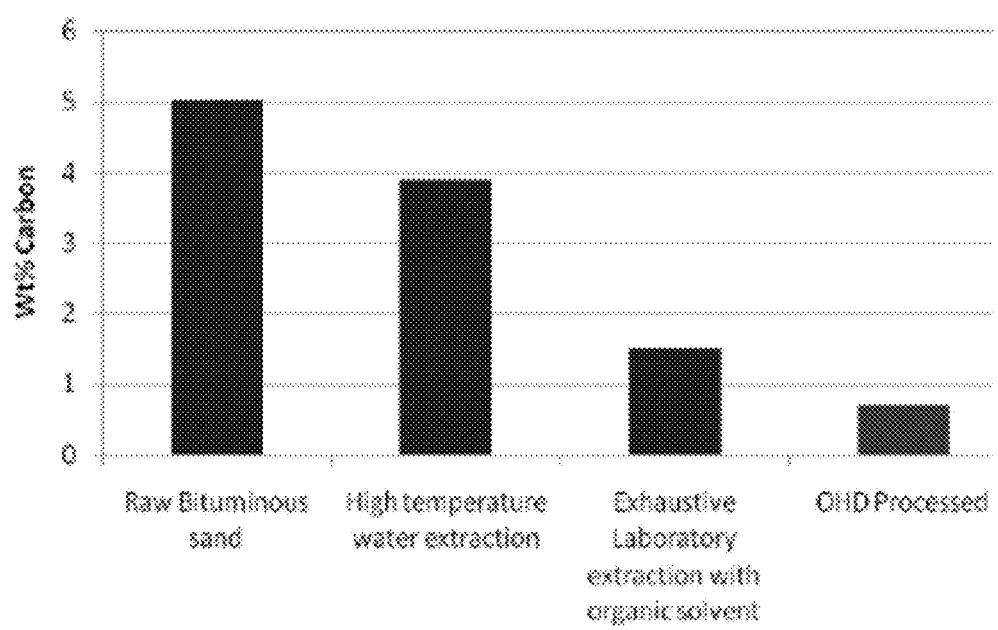
FIG. 4 is a graph comparing the carbon remaining after the processing of bituminous sand using three methods of carbon removal.

Table 2 summarizes the analysis of the insoluble products for each processing method. FIG. 4 is a bar graph summarizing the percentage of carbon remaining in the bituminous sand samples after treatment with the various methods to remove the bituminous materials from the inorganic sand matrix. These data illustrate that about 86% of the carbon initially present in the bituminous sand was removed by OHD processing, compared with 23% removed with superheated water alone and 69% removed by exhaustive laboratory extraction with organic solvent ($CH_2Cl_2$).

TABLE 2

ANALYSIS OF INSOLUBLE PRODUCTS

|  | Raw Bituminous sand | Superheated water extraction | Exhaustive Laboratory extraction with organic solvent | OHD processed |
|---|---|---|---|---|
| % Residual after processing | NA | 91 | 89.4 | 88.8 |
| High temperature Ash (Wt %) | 86.3 | 92.5 | 94.9 | 95.6 |
| C (Wt %) | 5.03 | 3.89 | 1.52 | 0.71 |
| H (Wt %) | 0.67 | 0.56 | <0.5 | <0.5 |
| N (Wt %) | <0.5 | <0.5 | <0.5 | <0.5 |

Figure 5:
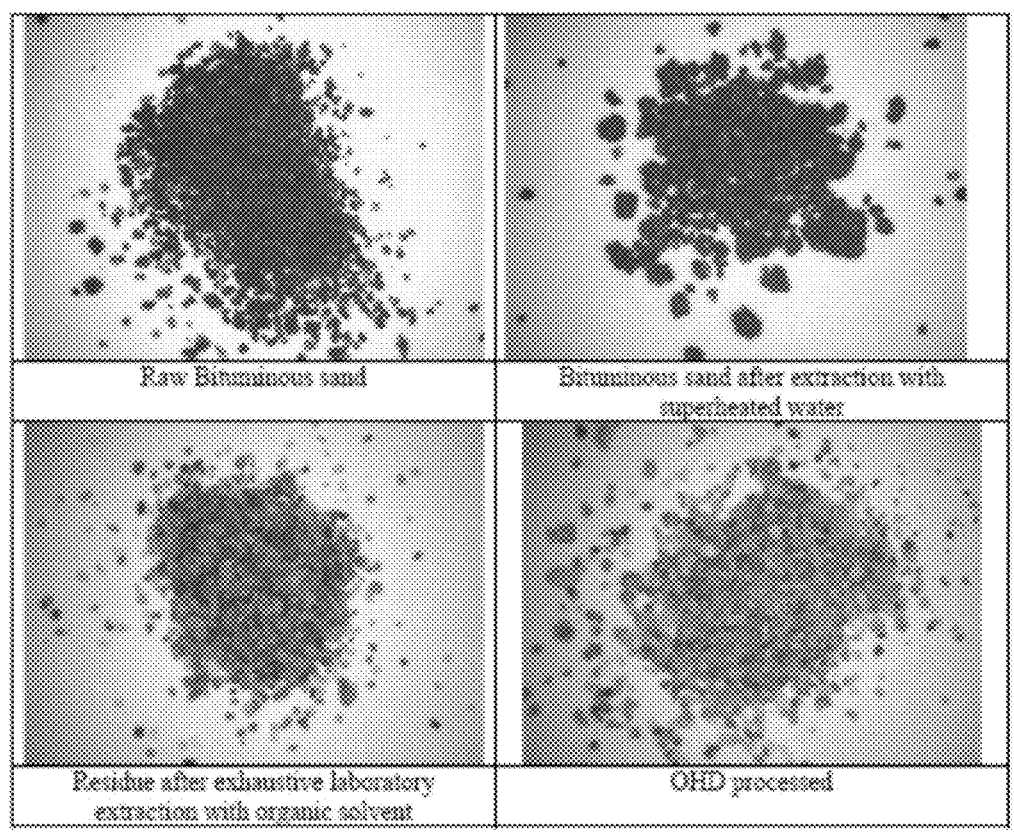
FIG. 5 are photographs of bituminous sand samples before and after processing using three methods of carbon removal.
Figure 6:
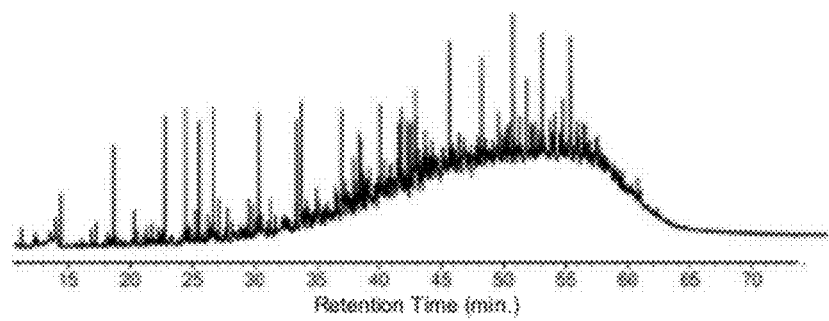
FIG. 6 is a graph summarizing results of a GC-MS analysis of organic products removed from bituminous sand using an OHD method and solvent extraction of the OHD liquor using methylene chloride.
Figure 7:
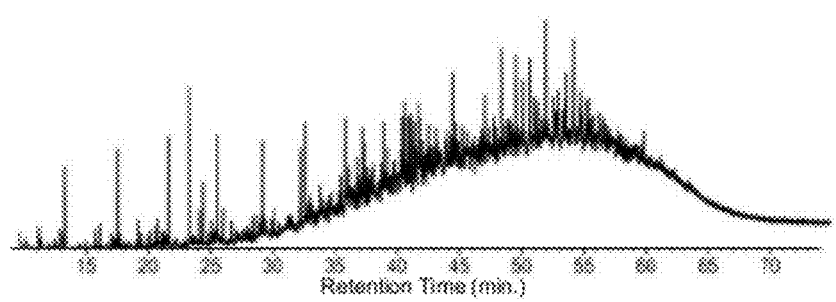
FIG. 7 is a graph summarizing results of a GC-MS analysis of organic products removed from bituminous sand using an OHD method and solvent extraction of the OHD liquor using ethyl acetate.
Figure 8:
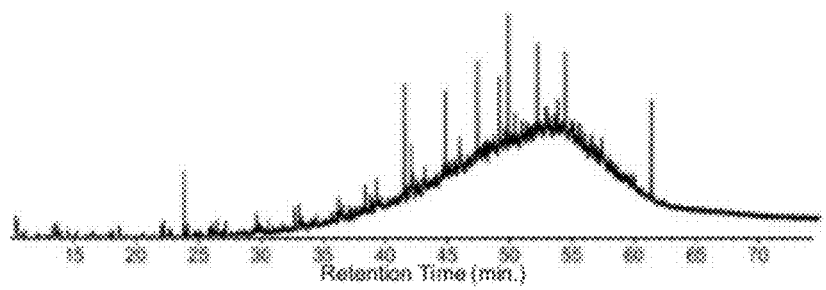
FIG. 8 is a graph summarizing results of a GC-MS analysis of organic products removed from bituminous sand using an OHD method and evaporative stripping of water from the OHD liquor.
Figure 9:
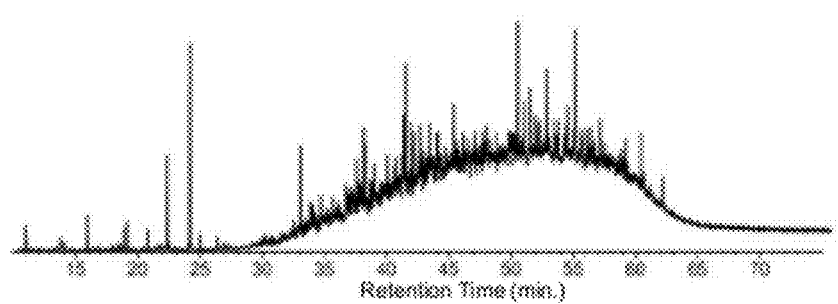
FIG. 9 is a graph summarizing results of a GC-MS analysis of organic products removed from bituminous sand using solvent extraction with methylene chloride.

FIG. 5 is a series of photographs of the bituminous sand samples before and after treatment with the various methods to remove the bituminous materials from the inorganic sand matrix samples. The residue derived from OHD processing is free-flowing, clean sand.

To evaluate the nature of the product obtained by OHD from this type of raw feedstock, bituminous product obtained from Athabasca bituminous sand was recovered and analyzed by GC-MS analysis using pyrolytic injection and in-situ methylation with tetramethyl ammonium hydroxide. These data were compared with data for the raw tar sand, from which the organic matter was simply distilled by flash pyrolysis.

Organic product was recovered from the primary OHD liquor resulting from the treatment of the bituminous sand by three techniques and the results of GC-MS analysis of the organic products was compared: (i) evaporative stripping (where water is removed from the product by distillation) (ii) solvent extraction with ethyl acetate and (iii) solvent extraction with methylene chloride ($CH_2Cl_2$). The GC-MS analysis data are summarized in FIGS. 6-10.

Figure 10:
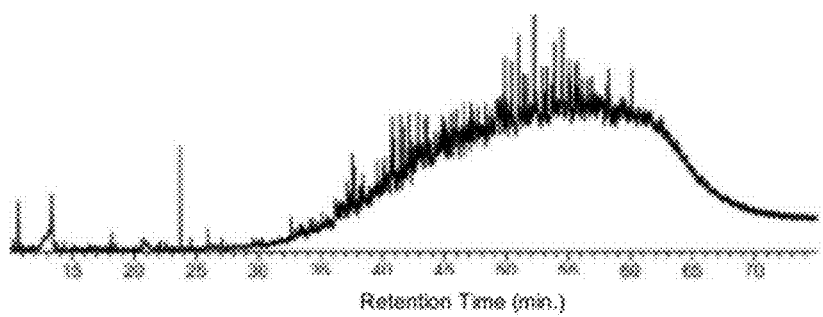
FIG. 10 is a graph summarizing results of a GC-MS analysis of organic products removed from bituminous sand using pyrolysis.

Data for the raw tar sands, shown in FIG. 10 are typical for this type of analysis of heavy oil and bitumen. The three OHD products, shown in FIGS. 6-8 indicate that the carbon content of the OHD liquor samples is comparable regardless of the method of extraction. Further, the carbon content of all OHD liquor samples (FIGS. 6-8) are consistent with the distillate of the raw tar sands, shown in FIG. 9, except that the OHD products contain discrete series of carboxylic acids and diacids that are much less apparent in the product from the distillate of the raw tar sands. This is expected due to the oxidative nature of the OHD process and does not significantly affect the usefulness of the derived "oil".

Example 2: OHD Processing of Canadian Athabasca Oil Sands

A bituminous sand sample of Athabasca oil sand was processed using the OHD method described herein above. The soluble products were recovered and analyzed using methods similar to those described in Example 1.

Figure 26:
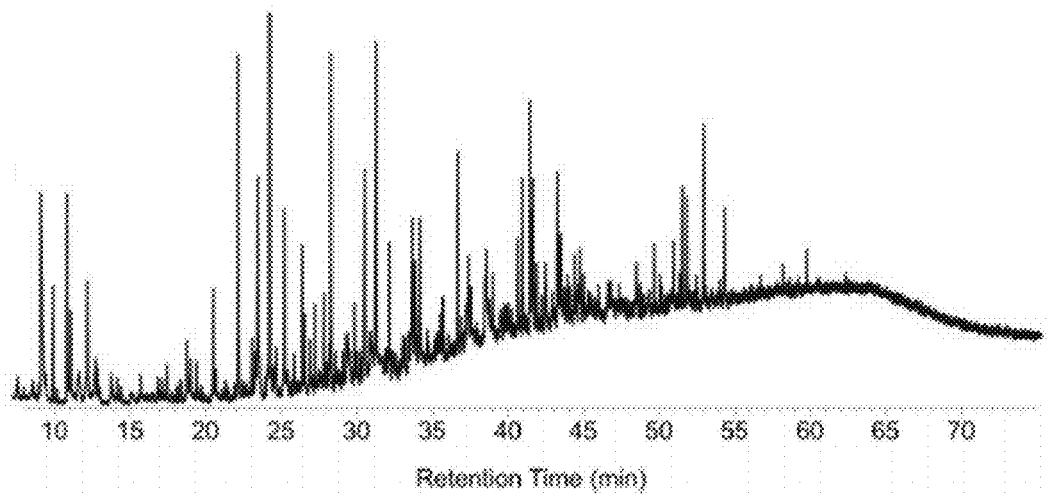
FIG. 26 is a graph summarizing results of a GC-MS analysis of organic products removed from bituminous sand using an OHD method and evaporative stripping of water from the OHD liquor.
Figure 27:
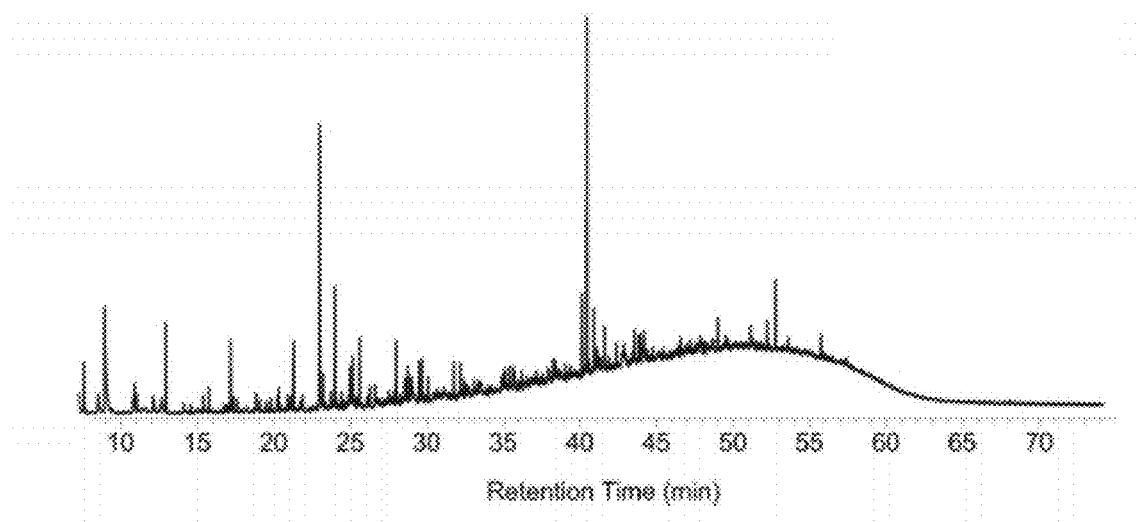
FIG. 27 is a graph summarizing results of a GC-MS analysis of organic products removed from bituminous sand using an OHD method and solvent extraction of the OHD liquor using ethyl acetate.
Figure 28:
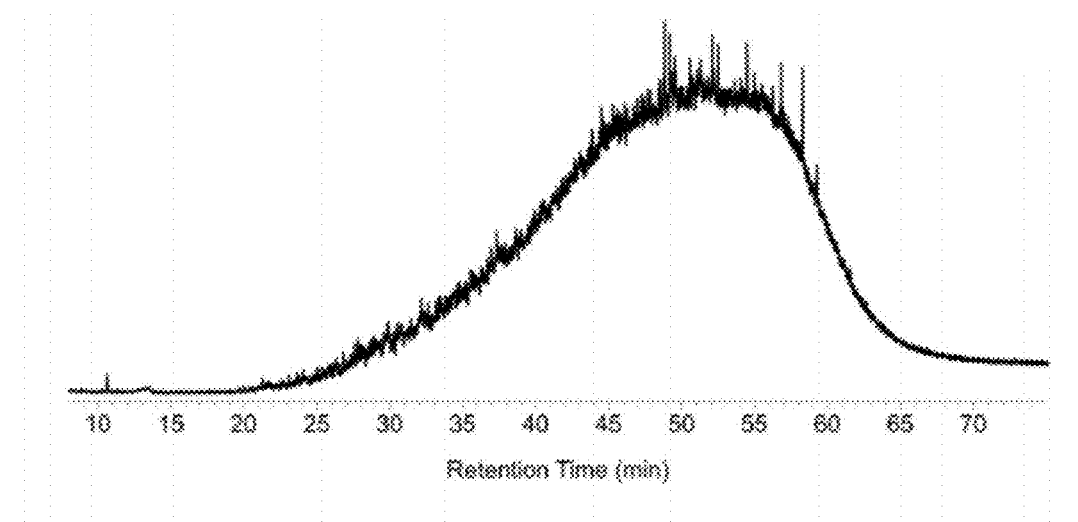
FIG. 28 is a graph summarizing results of a GC-MS analysis of organic products removed from bituminous sand using pyrolysis.

The results of the GC-MS analysis of the recovered organic products are summarized in FIGS. 26-28. The gas chromatographic mass spectrometric analysis of the raw bituminous sand are presented in FIG. 28 as the content of volatiles generated by flash distillation (i.e. Py-GC-MS) and OHD derived oils isolated by evaporative water removal (FIG. 26) and extraction of OHD liquor with ethyl acetate (FIG. 27).

Example 3: OHD Processing of Utah Sunnyside Oil Sands

A bituminous sand sample of Utah Sunnyside oil sand was processed using the OHD method described herein above. The soluble products were recovered and analyzed using methods similar to those described in Example 1.

Figure 29:
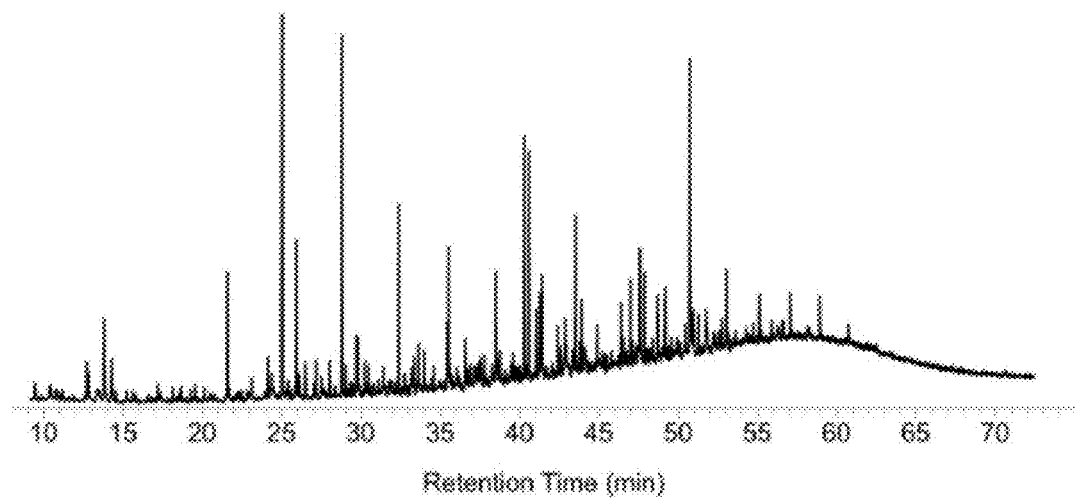
FIG. 29 is a graph summarizing results of a GC-MS analysis of organic products removed from bituminous sand using an OHD method and evaporative stripping of water from the OHD liquor.
Figure 30:
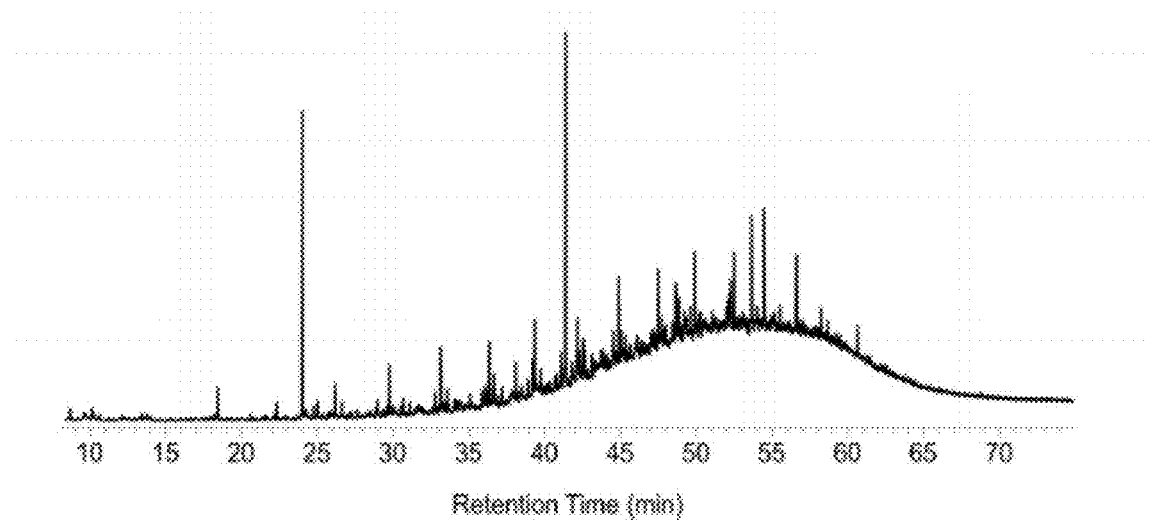
FIG. 30 is a graph summarizing results of a GC-MS analysis of organic products removed from bituminous sand using an OHD method and solvent extraction of the OHD liquor using ethyl acetate.
Figure 31:
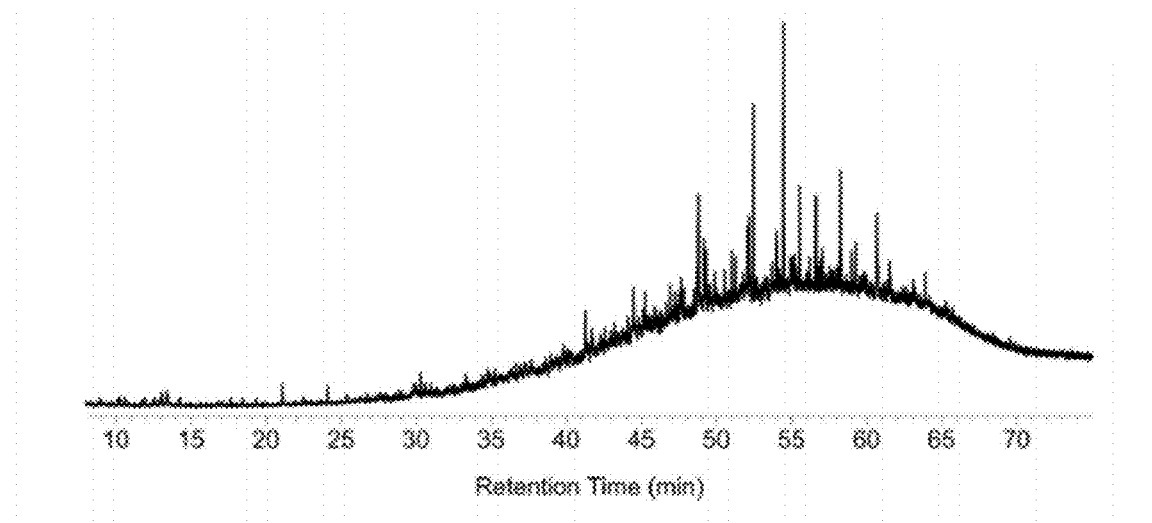
FIG. 31 is a graph summarizing results of a GC-MS analysis of organic products removed from bituminous sand using pyrolysis.

The results of the GC-MS analysis of the recovered organic products are summarized in FIGS. 29-31. The gas chromatographic mass spectrometric analysis of the raw bituminous sand are presented in FIG. 31 as the content of volatiles generated by flash distillation (i.e. Py-GC-MS) and OHD derived oils isolated by evaporative water removal (FIG. 29) and extraction of OHD liquor with ethyl acetate (FIG. 30).

Example 4: Organic Compounds Produced by OHD Processing of Illinois Coal

A sample of Illinois coal was processed using the OHD method described herein above. The soluble products were recovered and analyzed using methods similar to those described in Example 1. A total ion chromatogram summarizing the results of the GC-MS analysis of OHD liquor derived from the Illinois coal is provided in FIG. 11. The OHD liquor was pyrolyzed at a temperature of about 480° for about 10 seconds. Tetramethyl ammonium hydroxide was added to the OHD liquor for in situ derivatization of acidic oxygen-containing functional groups (phenol+carboxylate). A key listing the specific compounds associated with specific peaks is shown in Table 3:

TABLE 3

Specific Organic Compounds in OHD Liquor from Illinois Coal

| ID | Compound | Detailed Chromatogram Figure Number |
|---|---|---|
| A | 1,4-butenedioic acid | 12 |
| B | 1,4-butanedioic acid | 12 |
| C | 2-methyl butanedioic acid | 12 |
| D | benzoic acid | 13 |
| E | thiophene-2-carboxylic acid | 15 |
| F | thiophene-3-carboxylic acid | 15 |
| G | 1,5-pentanedioic acid | 12 |
| H | 1,2-dimethoxy benzene | 16 |
| I | 1,4-dimethoxy benzene | 16 |
| J | 1,3-dimethoxy benzene | 16 |
| K | 1,6-hexanedioic acid | 12 |
| L | Furan-3,4-dicarboxylic acid | 21 |
| M | 1,2,3-trimethoxybenzene | 21 |
| N | 2-methoxy benzoic acid | 13 |
| O | 1,7-heptanedioic acid | 12 |
| P | 3-methoxy benzoic acid | 13 |
| Q | Furan-2,5-dicarboxylic acid | 21 |
| R | 1,2,4-trimethoxybenzene | 21 |
| S | 4-methoxy benzoic acid | 13 |
| T | 1,2,3-propanetricarboxylic acid | 12 |
| U | 1,3,5-trimethoxybenzene | 21 |
| V | 1,2-benzene dicarboxylic acid | 14 |
| W | thiophene-2,3-dicarboxylic acid | 15 |
| X | 1,4-benzene dicarboxylic acid | 14 |
| Y | 1,3-benzene dicarboxylic acid | 14 |
| Z | thiophene-2,5-dicarboxylic acid | 15 |
| AA | 3,5-dimethoxy benzoic acid | 16 |
| BB | 3,4-dimethoxy benzoic acid | 16 |
| CC | methoxy benzene dicarboxylic acid (isomer undetermined) | 19 |
| CC | methoxy benzene dicarboxylic acid (isomer undetermined) | 19 |
| DD | 3,4,5-trimethoxy benzoic acid | None |
| EE | C14 Fatty acid (methyl ester) | 12 |
| CC | methoxy benzene dicarboxylic acid (isomer undetermined) | 19 |
| CC | methoxy benzene dicarboxylic acid (isomer undetermined) | 19 |
| FF | 1,3-benzodioxole-5,6-dicarboxylic acid | None |
| GG | 1,2,3-benzene tricarboxylic acid | 17 |
| HH | 1,2,4-benzene tricarboxylic acid | 17 |
| II | dimethoxy benzene dicarboxylic acid (isomer undetermined) | 18 |
| II | dimethoxy benzene dicarboxylic acid (isomer undetermined) | 18 |
| JJ | 1,3,5-benzene tricarboxylic acid | 17 |
| II | dimethoxy benzene dicarboxylic acid (isomer undetermined) | 18 |
| KK | C16 Fatty acid (methyl ester) | 12 |
| LL | Unknown (analog of X ?) | 19 |
| LL | Unknown (analog of X ?) | 19 |
| LL | Unknown (analog of X ?) | 19 |
| MM | Benzene tetracarboxylic acid (isomer undetermined) | 20 |
| NN | C18 Fatty acid (methyl ester) | 12 |
| MM | Benzene tetracarboxylic acid (isomer undetermined) | 20 |
| MM | Benzene tetracarboxylic acid (isomer undetermined) | 20 |
| OO | Unknown | None |

Figure 11:
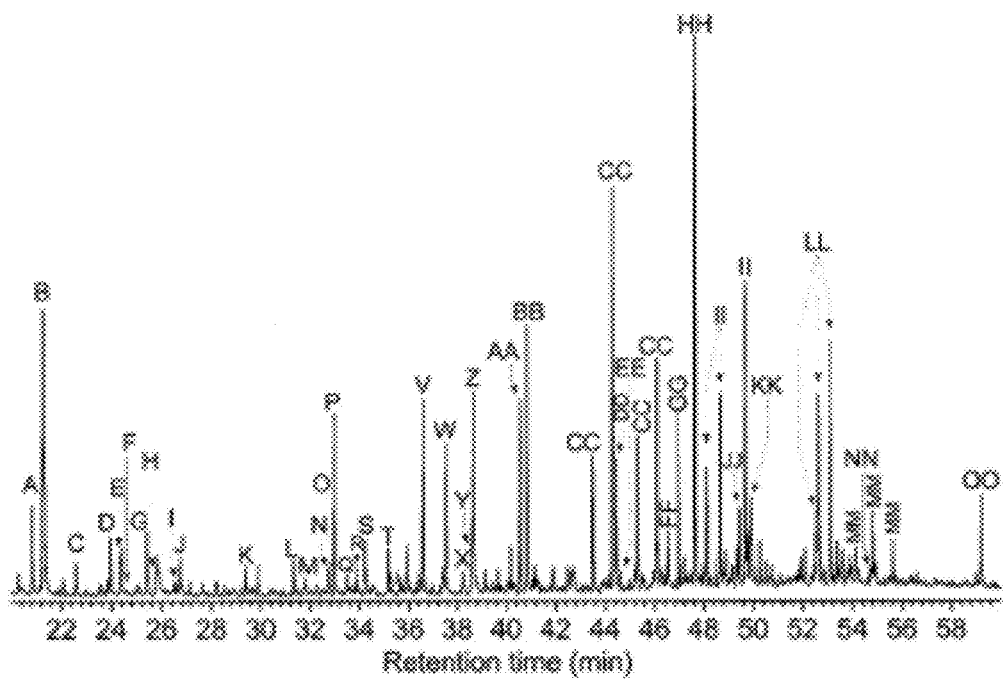
FIG. 11 is a total ion chromatogram illustrating the distribution of products observed by Py-GC-MS analysis of organic products removed from Illinois coal using an OHD method.
Figure 12:
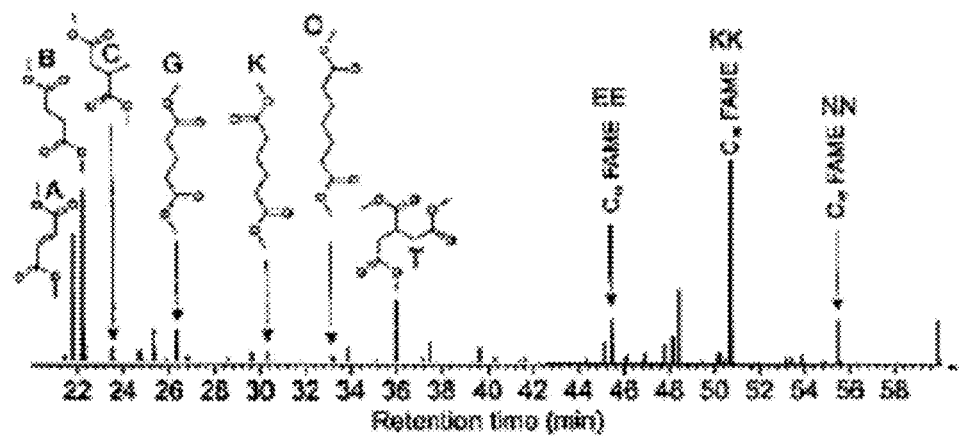
FIG. 12 is a multi-ion chromatogram illustrating the distribution of major aliphatic products observed by Py-GC-MS analysis of organic products removed from Illinois coal using an OHD method.
Figure 13:
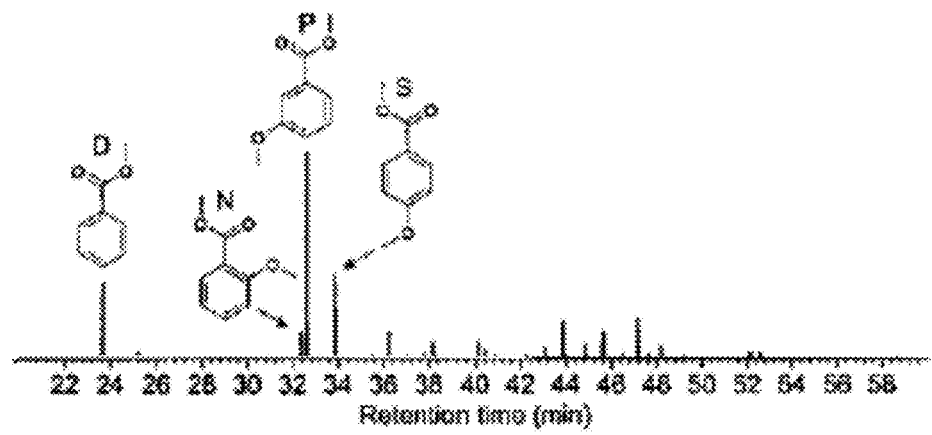
FIG. 13 is a multi-ion chromatogram illustrating the distribution of benzoic acid and mono methoxy benzoic acids observed by Py-GC-MS analysis of organic products removed from Illinois coal using an OHD method.
Figure 14:
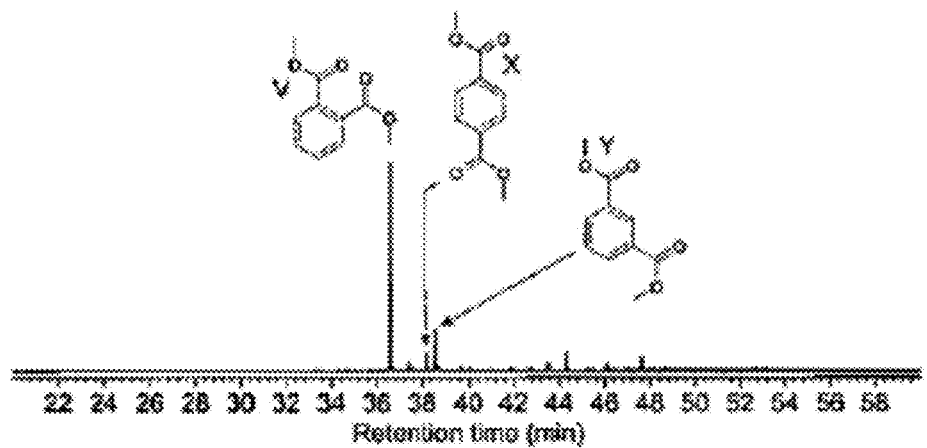
FIG. 14 is a single ion chromatogram illustrating the distribution of benzene dicarboxylic acids observed by Py-GC-MS analysis of organic products removed from Illinois coal using an OHD method.
Figure 15:
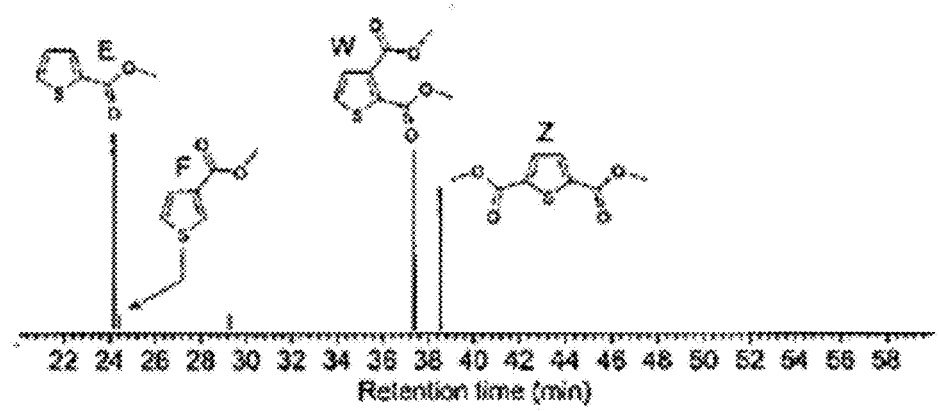
FIG. 15 is a multi-ion chromatogram illustrating the distribution of thiopene carboxylates and dicarboxylates observed by Py-GC-MS analysis of organic products removed from Illinois coal using an OHD method.
Figure 16:
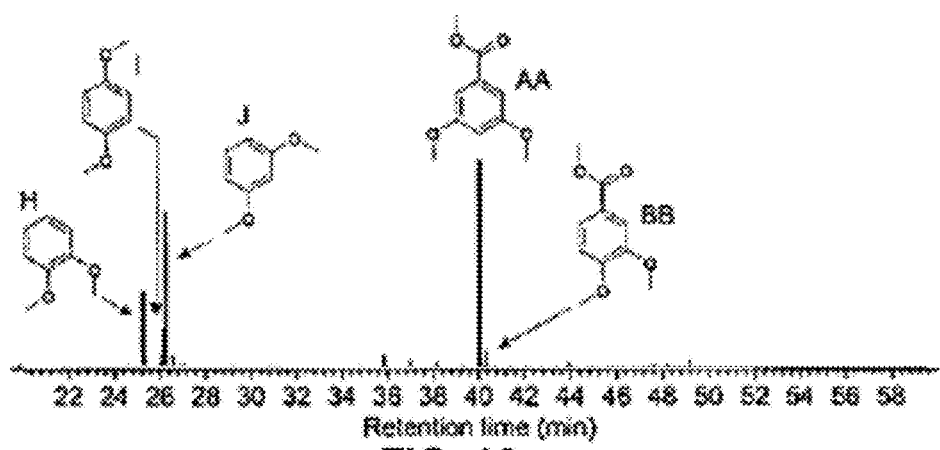
FIG. 16 is a single ion chromatogram illustrating the distribution of dimethoxy benzenes and dimethoxy benzoic acids observed by Py-GC-MS analysis of organic products removed from Illinois coal using an OHD method.
Figure 17:
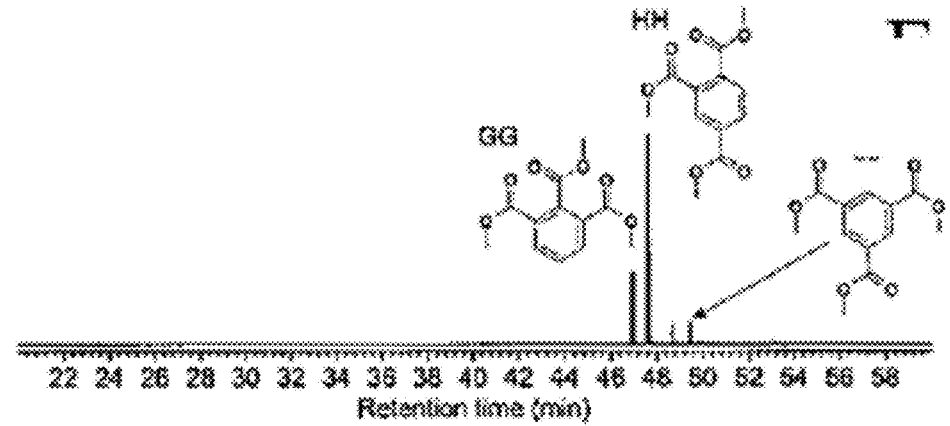
FIG. 17 is a single ion chromatogram illustrating the distribution of benzene tricarboxylic acids observed by Py-GC-MS analysis of organic products removed from Illinois coal using an OHD method.
Figure 18:
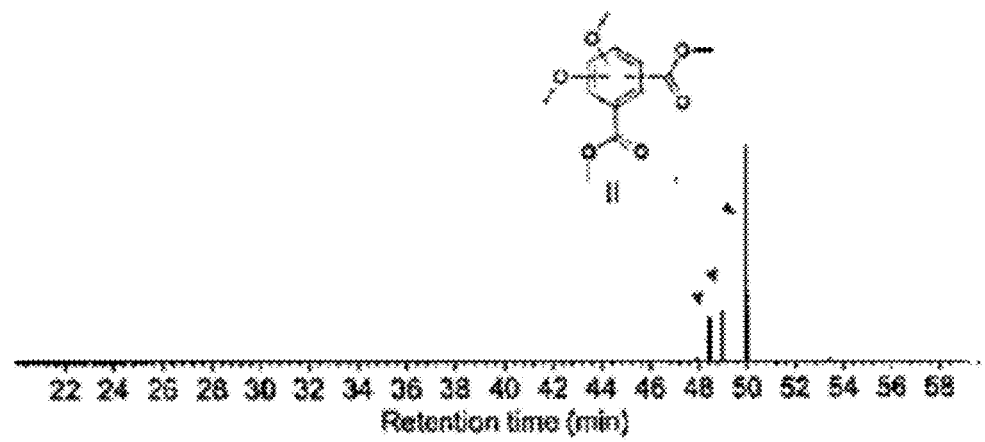
FIG. 18 is a single ion chromatogram illustrating the distribution of dimethoxy benzene dicarboxylic acids observed by Py-GC-MS analysis of organic products removed from Illinois coal using an OHD method.
Figure 19:
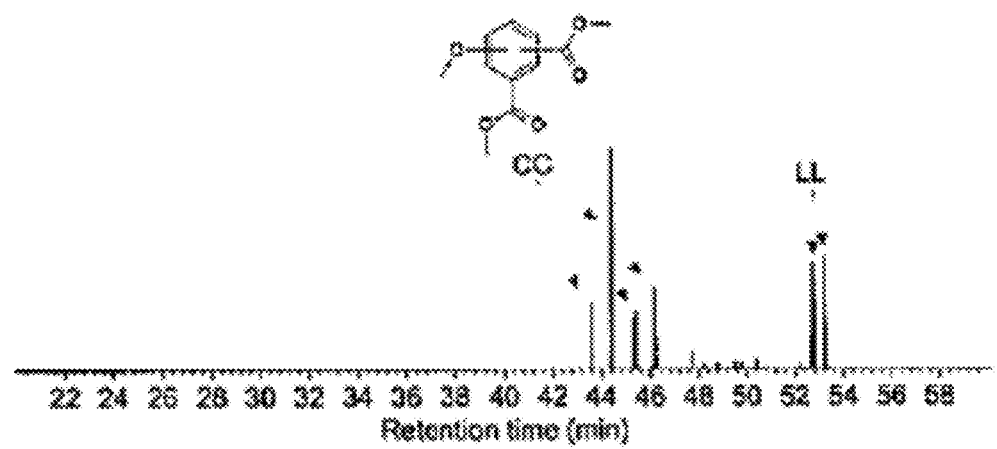
FIG. 19 is a multi-ion chromatogram illustrating the distribution of monomethoxy benzene dicarboxylic acids and unidentified analogs observed by Py-GC-MS analysis of organic products removed from Illinois coal using an OHD method.
Figure 20:
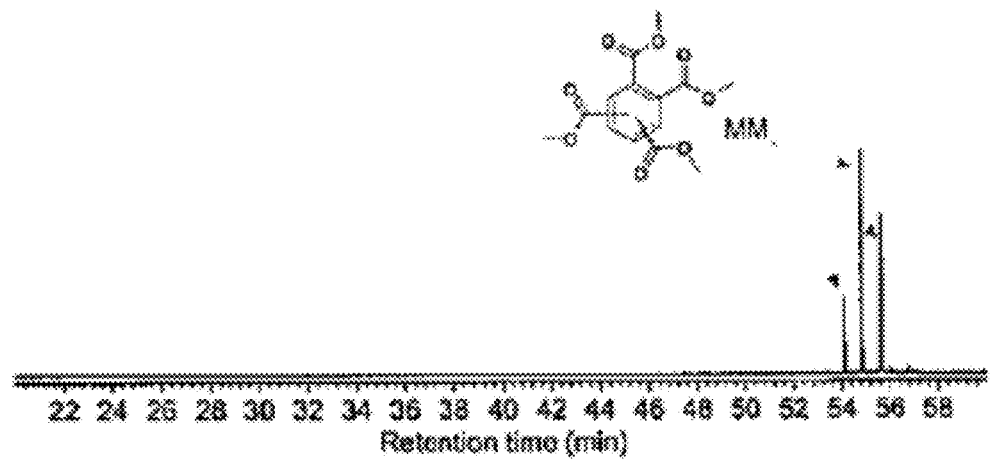
FIG. 20 is a single ion chromatogram illustrating the distribution of benzene tetra carboxylic acids observed by Py-GC-MS analysis of organic products removed from Illinois coal using an OHD method.
Figure 21:
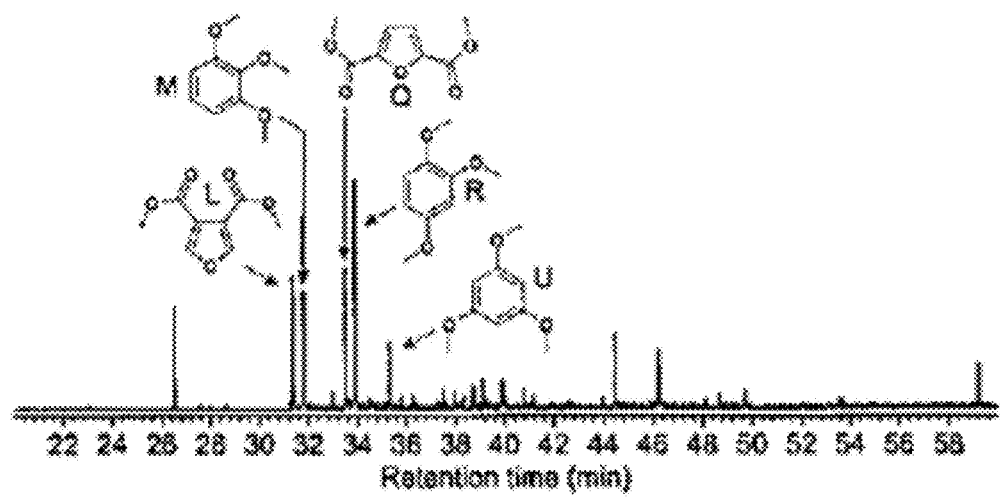
FIG. 21 is a multi-ion chromatogram illustrating the distribution of trimethoxy benzenes and furan dicarboxylic acids observed by Py-GC-MS analysis of organic products removed from Illinois coal using an OHD method.

FIGS. 12-21 are single and multi-ion chromatograms extracted from the total ion chromatogram of FIG. 11, illustrating the observed distributions of products of specific structural families. FIG. 12 is a multi-ion chromatogram (m/z=74+85+87+127) illustrating the distribution of major aliphatic products. FIG. 13 is a multi-ion chromatogram (m/z=105+135) illustrating the distribution of benzoic acid and mono methoxy benzoic acids. FIG. 14 is a single ion chromatogram (m/z=163) illustrating the distribution of benzene dicarboxylic acids. FIG. 15 is a multi-ion chromatogram (m/z=111+200) illustrating the distribution of thiophene carboxylates and dicarboxylates. FIG. 16 is a single ion chromatogram (m/z=138) illustrating the distribution of dimethoxy benzenes and dimethoxy benzoic acids. FIG. 17 is a single ion chromatogram (m/z=221) illustrating the distribution of benzene tricarboxylic acids. FIG. 18 is a single ion chromatogram (m/z=223) illustrating the distribution of dimethoxy benzene dicarboxylic acids. FIG. 19 is a multi-ion chromatogram (m/z=193+251) illustrating the distribution of monomethoxy benzene dicarboxylic acids and unidentified analogs. FIG. 20 is a single ion chromatogram (m/z=279) illustrating the distribution of benzene tetra carboxylic acids. FIG. 21 is a multi-ion chromatogram (m/z=168+184) illustrating the distribution of trimethoxy benzenes and furan dicarboxylic acids.

Example 5: Organic Compounds Produced by OHD Processing of Lignins

Figure 22:
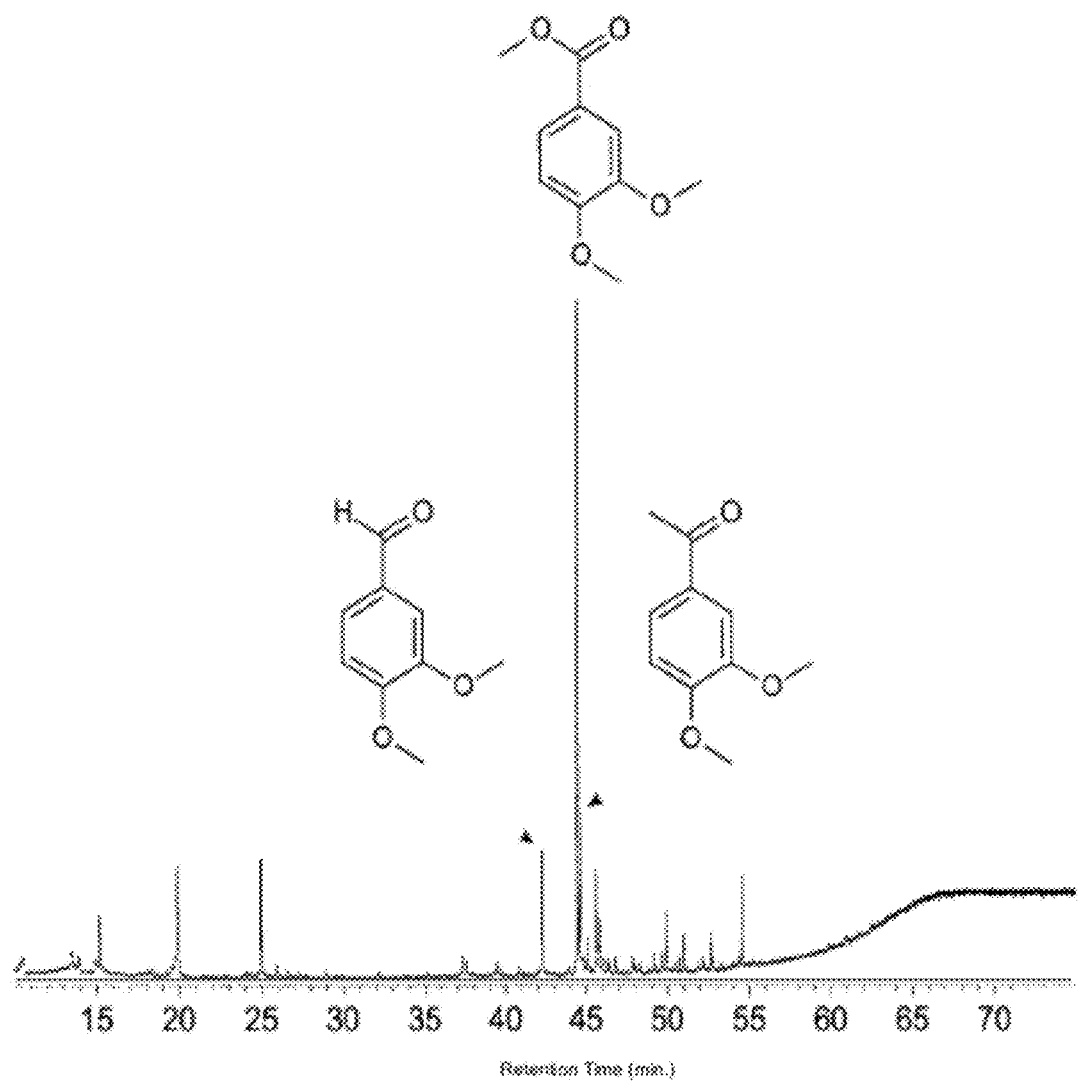
FIG. 22 is a total ion chromatogram illustrating the distribution of products observed by Py-GC-MS analysis of organic products removed from soft wood (conifer) lignin using an OHD method.
Figure 23:
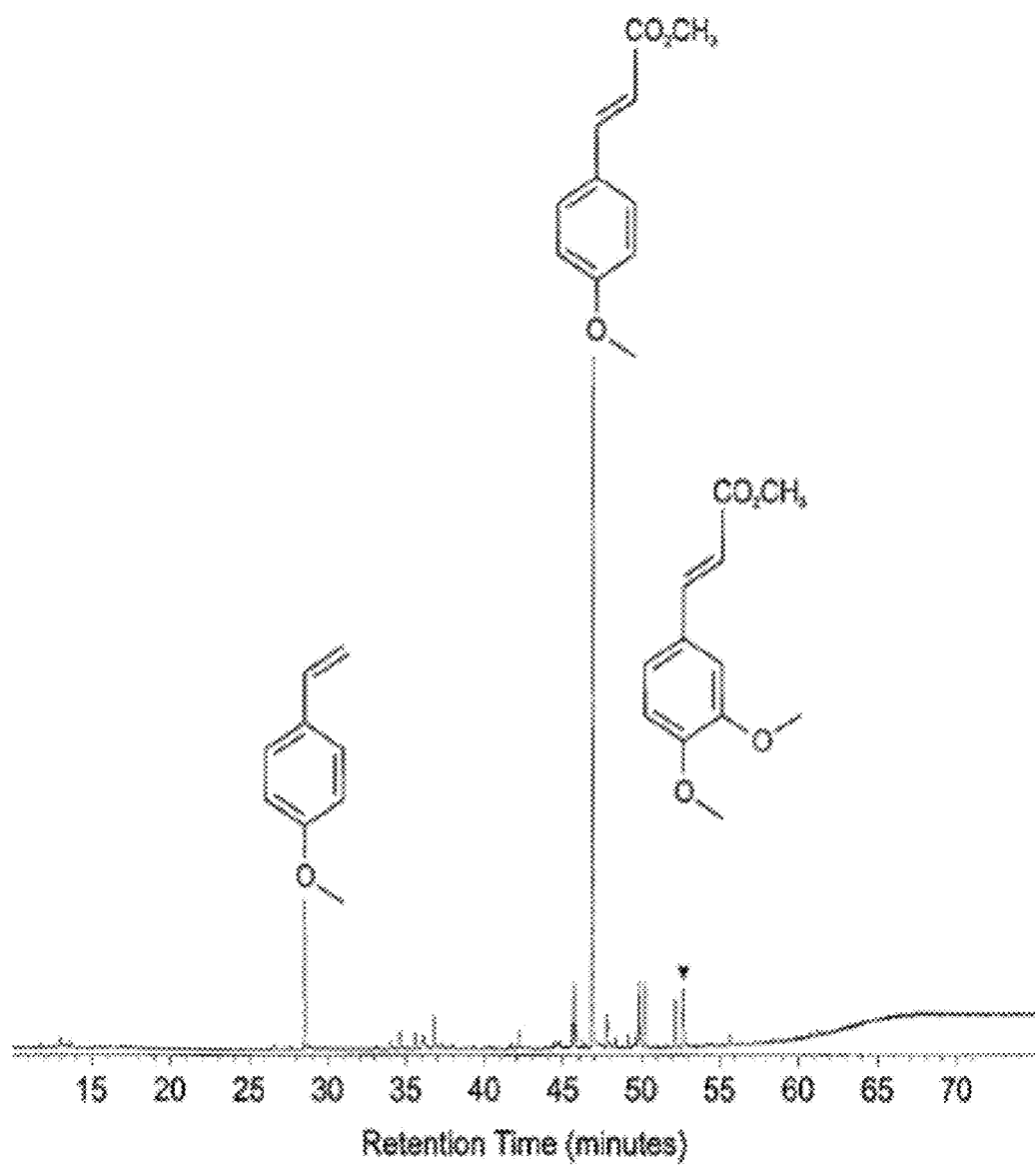
FIG. 23 is a total ion chromatogram illustrating the distribution of products observed by Py-GC-MS analysis of organic products removed from bamboo using an OHD method.

A sample of soft wood (conifer) lignin was processed using the OHD method described herein above. A second sample of lignin-rich grass (bamboo) was also processed using the OHD method described herein above. The soluble products were recovered and analyzed using methods similar to those described in Example 1. A total ion chromatogram summarizing the results of the GC-MS analysis of OHD liquor derived from the conifer lignin is provided in FIG. 22. A total ion chromatogram summarizing the results of the GC-MS analysis of OHD liquor derived from the bamboo lignin is provided in FIG. 23.

Example 6: Organic Compounds Produced by OHD Processing of Carbonaceous Shale

Figure 24:
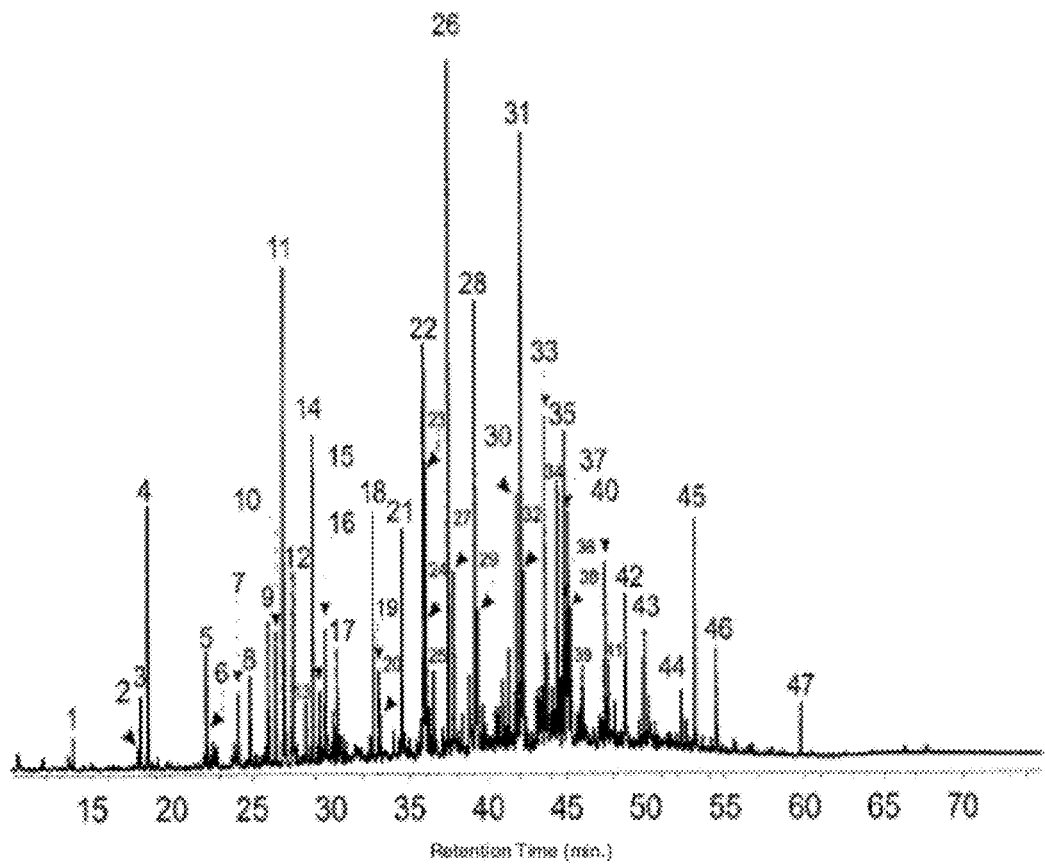
FIG. 24 is a total ion chromatogram illustrating the distribution of products observed by Py-GC-MS analysis of organic products removed from carbonaceous shale using an OHD method.

A sample of carbonaceous shale was processed using the OHD method described herein above. The soluble products were recovered and analyzed using methods similar to those described in Example 1. A total ion chromatogram summarizing the results of the GC-MS analysis of OHD liquor derived from the carbonaceous shale is provided in FIG. 24. Tetramethyl ammonium hydroxide was added to the OHD liquor for in situ derivatization of acidic oxygen-containing functional groups (phenol+carboxylate). A key listing the specific compounds associated with specific peaks is shown in Table 4:

TABLE 4

Specific Organic Compounds in OHD Liquor from Carbonaceous Shale

| ID | Compound |
|---|---|
| 1 | Pentanoic acid methyl ester |
| 2 | Hexenoic acid methyl ester |
| 3 | Hexanoic acid methyl ester |
| 4 | Methoxy Benzene |
| 5 | Heptanoic acid methyl ester |
| 6 | Hepteneoic acid methyl ester |
| 7 | 4-Oxo-pentanoic acid methyl ester |
| 8 | Butanedioic acid methyl ester (succinic acid di methyl ester) |
| 9 | Octanoic acid methyl ester |
| 10 | Benzoic acid methyl ester |
| 11 | Phenol |

TABLE 4-continued

Specific Organic Compounds in OHD Liquor from Carbonaceous Shale

| ID | Compound |
|---|---|
| 12 | 2-Methoxy phenol (Guaiacol) |
| 13 | 5-Oxo-hexanoic acid methyl ester |
| 14 | 1,2-Dimethoxy benzene + Pentanedioic acid dimethyl ester |
| 15 | 1,4-Dimethoxy benzene |
| 16 | Nonanoic acid methyl ester |
| 17 | 2 Hydroxy benzoic acid methyl ester |
| 18 | Hexanedioic acid dimethyl ester + 6-Oxo Heptanoic acid methyl ester |
| 19 | Decanoic acid methyl ester |
| 20 | unknown |
| 21 | 4-Methoxy benzaldehyde |
| 22 | 3-Methoxy benzoic acid methyl ester |
| 23 | Heptanedioic acid dimethyl ester |
| 24 | 7-Oxo Octanoic acid methyl ester |
| 25 | 2-Methoxy benzoic acid methyl ester |
| 26 | 4-Methoxy benzoic acid methyl ester |
| 27 | 4-Methoxy acetophenone |
| 28 | Octanedioic acid dimethyl ester |
| 29 | 8-Oxo nonanoic acid methyl ester |
| 30 | 1,3-benzene dicarboxylic acid dimethyl ester |
| 31 | Nonanedioic acid dimethyl ester |
| 32 | 9-Oxo decanoic acid methyl ester |
| 33 | 3-Hydroxy benzoic acid methyl ester |
| 34 | 3,4-Dimethoxy benzoic acid methyl ester |
| 35 | Decanedioic acid dimethyl ester |
| 36 | 10-Oxo undecanoic acid methyl ester |
| 37 | 2-Hydroxy-1,4-benzene dicarboxylic acid dimethyl ester |
| 38 | 4-Hydroxy benzoic acid methyl ester |
| 39 | Unknown dicarboxylic acid |
| 40 | Undecanedioic acid dimethyl ester |
| 41 | Unknown |
| 42 | Unknown Oxo terpenoid |
| 43 | Hexdecanoic acid methyl ester + dodecanoic diacid dimethyl ester |
| 44 | Tridecanedioic acid dimethyl ester |
| 45 | 1,3,5 benzene tricarboxylic acid trimethyl ester |
| 46 | Octadecanoic acid methyl ester |
| 47 | Octadecanoic acid butyl ester |

Figure 25:
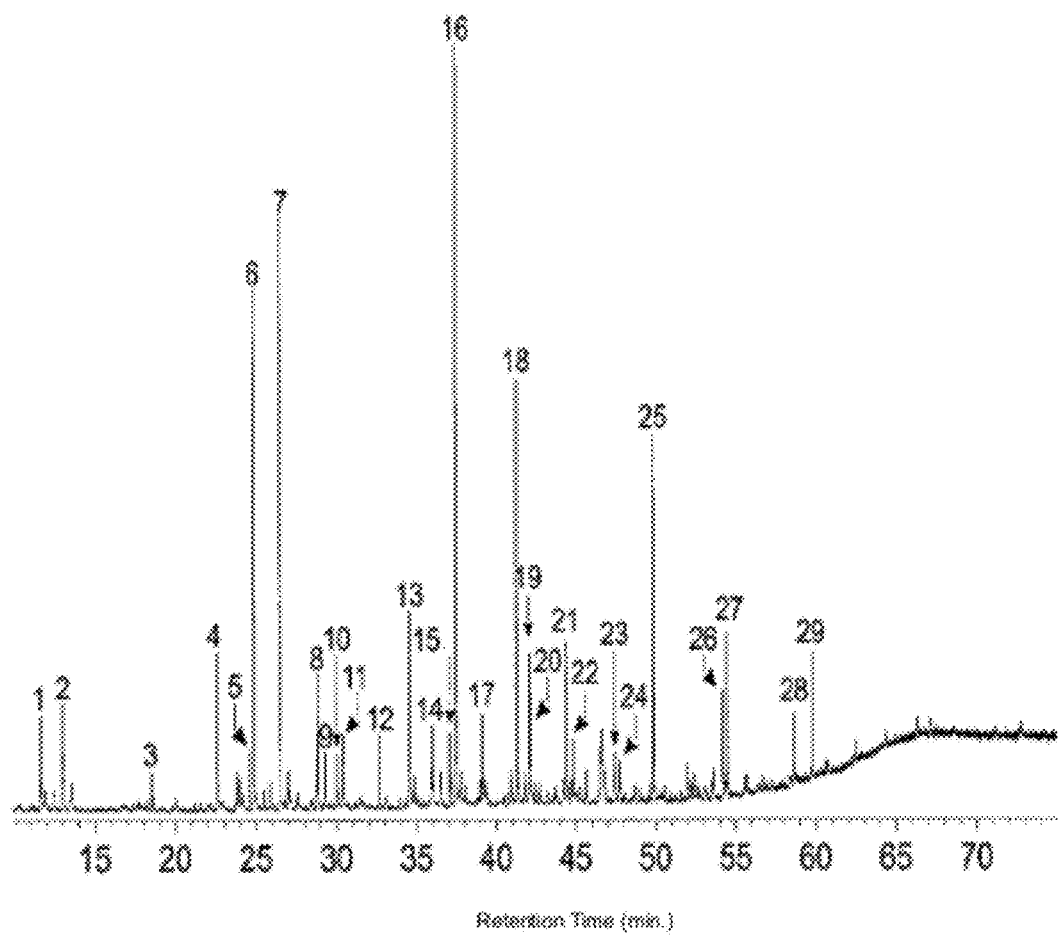
FIG. 25 is a total ion chromatogram illustrating the distribution of products observed by Py-GC-MS analysis of organic products removed from sugar cane bagasse using an OHD method.

Example 7: Organic Compounds Produced by OHD Processing of Sugar Cane Bagasse A sample of sugar cane bagasse was processed using the OHD method described herein above. The soluble products were recovered and analyzed using methods similar to those described in Example 1. A total ion chromatogram summarizing the results of the GC-MS analysis of OHD liquor derived from the sugar cane bagasse is provided in FIG. 25. Tetramethyl ammonium hydroxide was added to the OHD liquor for in situ derivatization of acidic oxygen-containing functional groups (phenol+carboxylate). A key listing the specific compounds associated with specific peaks is shown in Table 5:

TABLE 5

Specific Organic Compounds in OHD Liquor from Sugar Cane Bagasse

| ID | Compound |
|---|---|
| 1 | Hydroxy acetic acid |
| 2 | Methoxy acetic acid |
| 3 | Methyoxy benzene |
| 4 | Furan carboxylic acid methyl ester (isomer unknown) |
| 5 | Unknown |
| 6 | Succinic acid |
| 7 | Benzoic acid |
| 8 | Pentane dioic acid |
| 9 | 1,4-dirnethoxy benzene |
| 10 | Phenyl acetic acid |
| 11 | 2-Hydroxy benzoic acid + unknown |
| 12 | Hexane dioic acid |
| 13 | 4-Methoxy benzaldehyde |
| 14 | Heptane dioic acid + 3 methoxy benzoic acid |
| 15 | Unknown |
| 16 | 4 methoxy benzoic acid |
| 17 | Octane dioic acid |
| 18 | Terephthalic acid |
| 19 | Nonane dioic acid |
| 20 | 3,4-dimethoxy benzaldehyde |
| 21 | 3,4-dimethoxy benzoic acid |
| 22 | Tetradecanoic acid |
| 23 | C15 carboxylic acid (unknown isomer) |
| 24 | 3,4,5-trimethoxy benzoic acid |
| 25 | Hexadecanolic acid |
| 26 | Octadecenoic acid (unknown double bond isomer) |
| 27 | Octadecanoic acid |
| 28 | Eicosanoic acid |
| 29 | Unknown fatty acid |

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

The invention claimed is:

1. A process for solubilizing an organic solid contained within a composite material comprising an organic solid and an inorganic matrix, the process comprising: below the critical temperature of water, reacting the composite material with a non-gaseous oxidant in superheated, non-gaseous water to form an aqueous mixture comprising at least one solubilized organic solute, wherein the non-gaseous oxidant is present at or below its solubility limit in the superheated, non-gaseous water such that no gas phase is present during the reaction.

2. The process of claim 1, wherein the oxidant is molecular oxygen ($O_2$).

3. The process of claim 2, wherein the molecular oxygen is supplied by any method selected from the group consisting of:
in situ decomposition of hydrogen peroxide;
fractional distillation of liquefied air;
electrolysis of water;
transfer from a stored oxygen supply;
membrane separation from air; and
any combination thereof.

4. The process of claim 3, wherein the molecular oxygen is supplied by in situ decomposition of hydrogen peroxide.

5. The process of claim 1, wherein the composite material is contacted with the oxidant in a superheated water at a temperature ranging from about 100° C. to about 370° C.

6. The process of claim 5, wherein the composite material is contacted with the oxidant in superheated water at a temperature ranging from about 200° C. to about 350° C.

7. The process of claim 1, wherein the composite material is contacted with the oxidant in superheated water at a pressure ranging from about 100 kPa to about 22 MPa.

8. The process of claim 7, wherein the composite material is contacted with the oxidant in superheated water at a pressure ranging from about 1.5 MPa to about 17 MPa.

9. The process of claim 8, wherein the composite material is contacted with the oxidant in superheated water at a pressure ranging from about 12 MPa to about 16 MPa.

10. The process of claim 1, wherein the composite material is selected from the group consisting of coal, bituminous sand, carbonaceous shale, biomass, and any mixture thereof.

11. The process of claim 10, wherein the composite material is biomass, and wherein at least one solubilized organic solute comprises at least one of a low molecular weight sugar, an oxidized low molecular weight sugar, and any combination thereof.

12. The process of claim 1, wherein the composite material is contacted with the oxidant in the superheated water within a reactor, wherein the composite material, oxidant, and superheated water are maintained in a non-gaseous phase to inhibit the formation of a head space within the reactor.

13. The process of claim 1, further comprising chilling the aqueous mixture to a temperature of about 20° C.

14. The process of claim 1, wherein the aqueous mixture has a pH ranging from about 1 to about 5.

15. The process of claim 1, wherein the aqueous mixture comprises at least 50% of the organic solid from the composite material.

16. The process of claim 15, wherein the aqueous mixture comprises at least 90% of the organic solid from the composite material.

17. The process of claim 16, wherein the aqueous mixture comprises at least 95% of the organic solid from the composite material.

18. The process of claim 1, further comprising:
pulverizing the composite material; and
combining the pulverized composite material with water to form a slurry prior to contacting the composite material with the oxidant in the superheated water.

19. The process of claim 18, wherein the pulverized composite material has a particle size ranging from about 60 mesh to about 20 mesh.

20. The solubilized organic solute of the process of claim 1.

21. A process for solubilizing an organic solid contained within a solid composite material comprising an organic solid and an inorganic matrix, the process comprising: below a temperature of 370° C., contacting the solid composite material with a non-gaseous oxidant in superheated, non-gaseous water to form an aqueous mixture comprising at least one solubilized organic solute.

* * * * *